(12) United States Patent
Takie et al.

(10) Patent No.: US 12,745,347 B2
(45) Date of Patent: Sep. 22, 2026

(54) IMAGE PICKUP UNIT AND ENDOSCOPE

(71) Applicant: OLYMPUS MEDICAL SYSTEMS CORP., Tokyo (JP)

(72) Inventors: Shuichi Takie, Hachioji (JP); Takuro Horibe, Funabashi (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 363 days.

(21) Appl. No.: 18/371,592

(22) Filed: Sep. 22, 2023

(65) Prior Publication Data

US 2024/0008718 A1 Jan. 11, 2024

Related U.S. Application Data

(63) Continuation of application No. PCT/JP2021/020824, filed on Jun. 1, 2021.

(51) Int. Cl.

*A61B 1/00* (2006.01)
*A61B 1/04* (2006.01)
*H05K 1/02* (2006.01)

(52) U.S. Cl.

CPC ........ *H05K 1/0284* (2013.01); *A61B 1/00114* (2013.01); *A61B 1/04* (2013.01)

(58) Field of Classification Search

CPC ....... A61B 1/00; A61B 1/051; A61B 1/00114; H05K 1/0284; H04N 23/57
USPC .......................................................... 174/255
See application file for complete search history.

(56) References Cited

U.S. PATENT DOCUMENTS

2009/0021618 A1 1/2009 Schwarz et al.

FOREIGN PATENT DOCUMENTS

| | | |
|---|---|---|
| JP | 2009-027709 A | 2/2009 |
| JP | 2011-081319 A | 4/2011 |
| JP | 2015-080675 A | 4/2015 |
| JP | 2017-023234 A | 2/2017 |
| WO | 2018/021061 A1 | 2/2018 |

OTHER PUBLICATIONS

International Search Report dated Aug. 24, 2021 received in PCT/JP2021/020824.

*Primary Examiner* — Tremesha W Burns
(74) *Attorney, Agent, or Firm* — Scully, Scott, Murphy & Presser, P.C.

(57) ABSTRACT

An image pickup unit includes: an image pickup device; a flat circuit board; a three-dimensional circuit board; plural electronic components; and plural cables, in which the three-dimensional circuit board includes: a first surface; a second surface; a third surface; a fourth surface; a fifth surface; and a sixth surface, in which on one of the first surface to the sixth surface, a recessed portion is formed and a connection terminal portion is formed in an inner surface of the recessed portion, one of the plural electronic components or the plural cables is mounted on or connected to the connection terminal portion, the recessed portion is formed, in a site where the first surface and the sixth surface cross each other, from the second surface toward the third surface, the recessed portion having a wall surface parallel to the second surface, and one of the electronic components is mounted.

17 Claims, 9 Drawing Sheets

IMAGE PICKUP UNIT AND ENDOSCOPE

CROSS REFERENCE TO RELATED APPLICATION

This application is a continuation application of PCT/JP2021/020824 on Jun. 1, 2021, the entire contents of which are incorporated herein by this reference.

BACKGROUND OF THE INVENTION

1. Field of the Invention

The present invention relates to an image pickup unit that acquires an image, and an endoscope to which the image pickup unit is applied.

2. Description of the Related Art

Conventionally, endoscopes configured with an insertion portion in an elongated tubular shape have widely been used in, for example, the medical field, the industrial field, and the like. Of such endoscopes, endoscopes for medical purpose used in the medical field have functions of observing and examining a state of a lesion site or the like by, for example, inserting the insertion portion equipped with an image pickup unit into a body cavity of a living body to acquire an image inside an internal organ or the like of the living body. Endoscopes for industrial purpose used in the industrial field are configured with functions of observing and inspecting the state of a scratch, corrosion, or the like by, for example, inserting the insertion portion equipped with the image pickup unit into an apparatus such as a jet engine, plant piping, or the like, or a machinery facility or the like to acquire an image inside the apparatus or the machinery facility.

A conventional image pickup unit in the form of this type is typically provided, for example, inside a distal end portion of the insertion portion of the endoscope. The image pickup unit in the conventional form is configured with an image pickup device, or the like that receives an optical image of a target that is formed by an image-forming optical lens unit and generates an image signal, and a circuit board to which the image pickup device is connected. An image signal processing circuit, a drive circuit, and the like, which are configured with electronic components, such as a capacitor and an IC chip, are mounted on the circuit board. A plurality of signal transmission cables, which perform inputting/outputting electric signals between the circuit board and a control device as external equipment, are connected to the circuit board by soldering or the like.

There has been a constant demand for downsizing and reduction in diameter of the conventional endoscope. To that end, downsizing of the image pickup unit itself applied to the endoscope has also concurrently been demanded. As means for achieving a downsized image pickup unit or endoscope while maintaining the conventional functions, expansion of the area for mounting electronic components, highly-dense mounting of components on a circuit board, or the like is conceived.

Thus, in recent years, as a form of the circuit board in the image pickup unit, a circuit board in a three-dimensional structure (hereinafter, referred to as a three-dimensional circuit board) has been designed. The three-dimensional circuit board achieves expansion of a mounting area by providing, on a surface, a connecting pattern for mounting electronic components and the like.

The image pickup unit and the endoscope in various forms, to which the three-dimensional circuit board of this type is applied, are proposed by Japanese Patent Application Laid-Open Publication No. 2017-23234, or the like.

The image pickup unit and the endoscope that are disclosed in the aforementioned Japanese Patent Application Laid-Open Publication No. 2017-23234 or the like include an image pickup device, a flat circuit board, and a three-dimensional circuit board, and the flat circuit board and the three-dimensional circuit board are configured in such a form as being fitted within a projection plane in an optical axis direction of the image pickup unit. A connecting pattern on an outer periphery surface of the three-dimensional circuit board is configured so as to allow connection with the flat circuit board, mounting of various electronic components, and connection of a signal transmission cable or the like. In this manner, downsizing or highly-dense mounting of components in the image pickup unit and the endoscope is achieved.

Meanwhile, in recent years, there has been an increasing demand for enhanced functionality in addition to the demand for downsizing and reduction in diameter of the image pickup unit and the endoscope as described above.

SUMMARY OF THE INVENTION

An image pickup unit of an aspect of the present invention includes: an image pickup device; a flat circuit board connected to a back surface of the image pickup device, a three-dimensional circuit board connected to a back surface of the flat circuit board; a plurality of electronic components mounted on the flat circuit board or the three-dimensional circuit board; and a plurality of cables connected to the three-dimensional circuit board, in which the three-dimensional circuit board includes: a first surface; a second surface substantially orthogonal to the first surface; a third surface facing opposite to the second surface; a fourth surface facing opposite to the first surface; a fifth surface facing the back surface of the flat circuit board; and a sixth surface facing opposite to the fifth surface, in which on at least one of the first surface to the sixth surface, a recessed portion is formed and a connection terminal portion is formed in a part of an inner surface of the recessed portion, at least one of the plurality of electronic components or the plurality of cables is mounted on or connected to the connection terminal portion of the recessed portion of the three-dimensional circuit board, the recessed portion is formed, in a site where the first surface and the sixth surface cross each other, from the second surface toward the third surface, the recessed portion having a wall surface parallel to the second surface, and at least one of the electronic components is mounted in the recessed portion.

An endoscope of an aspect of the present invention includes, inside a distal end portion of an insertion portion, an image pickup unit that includes: an image pickup device; a flat circuit board connected to a back surface of the image pickup device; a three-dimensional circuit board connected to a back surface of the flat circuit board, a plurality of electronic components mounted on the flat circuit board or the three-dimensional circuit board; and a plurality of cables connected to the three-dimensional circuit board, in which the three-dimensional circuit board includes: a first surface; a second surface substantially orthogonal to the first surface; a third surface facing opposite to the second surface; a fourth surface facing opposite to the first surface; a fifth surface facing the back surface of the flat circuit board; and a sixth surface facing opposite to the fifth surface, in which on at least one of the first surface to the sixth surface, a recessed portion is formed and a connection terminal portion is formed in a part of an inner surface of the recessed portion, at least one of the plurality of electronic components or the plurality of cables is mounted on or connected to the connection terminal portion of the recessed portion of the three-dimensional circuit board, the recessed portion is formed, in a site where the first surface and the sixth surface cross each other, from the second surface toward the third surface, the recessed portion having a wall surface parallel to the second surface, and at least one of the electronic components is mounted in the recessed portion.

DETAILED DESCRIPTION OF THE PREFERRED EMBODIMENT

Figure 1:
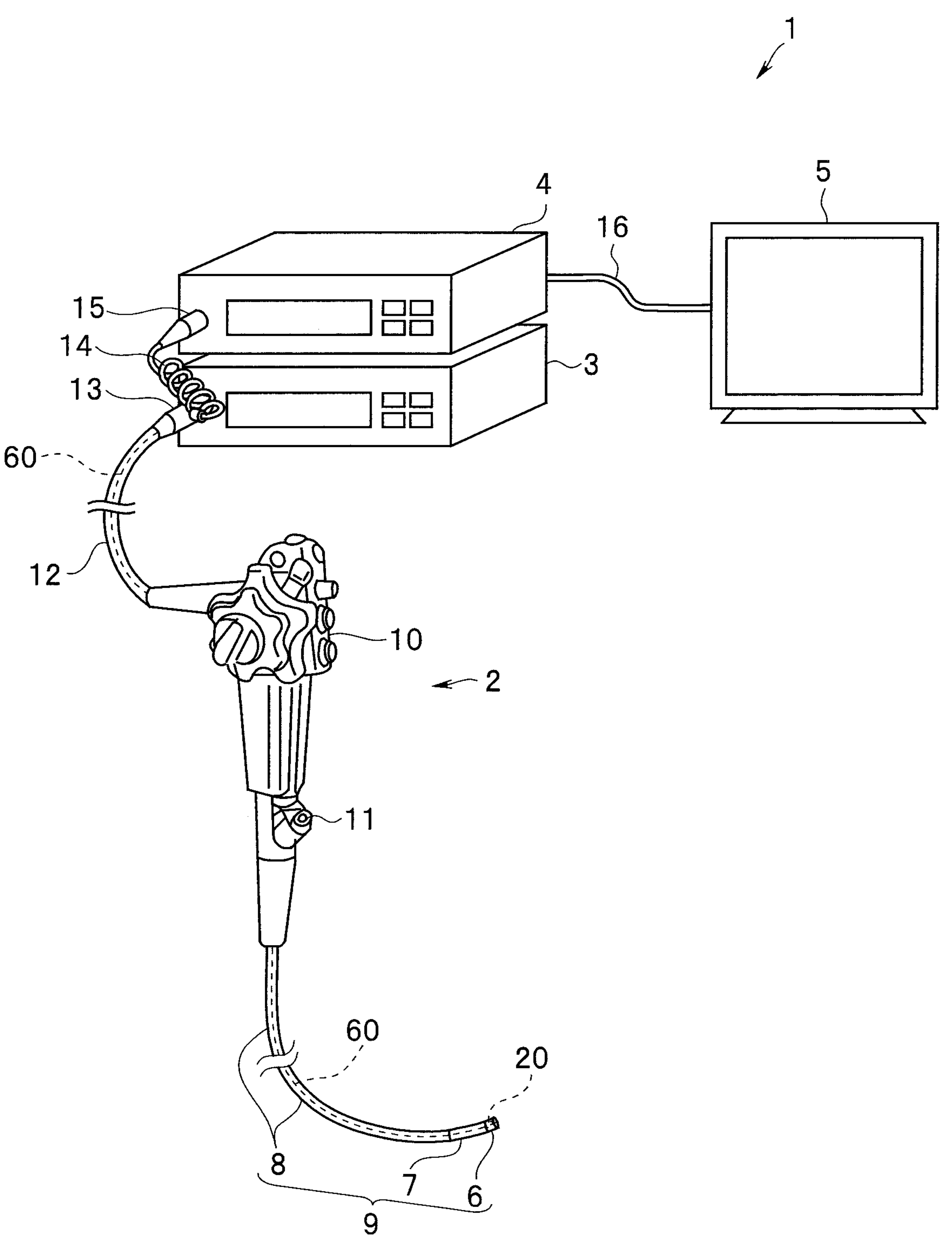
FIG. 1 is an outer appearance view showing an endoscope system including an endoscope to which an image pickup unit of an embodiment of the present invention is applied.

In general, to achieve enhanced functionality of an image pickup unit, electronic components mounted on a circuit board of the image pickup unit are increased in number or signal transmission cables or the like connected to the circuit board are increased in number, for example. Thus, the conventional configuration disclosed in the aforementioned Japanese Patent Application Laid-Open Publication No. 2017-23234 or the like alone cannot fully address recently increasing enhanced functionality of the image pickup unit and the endoscope, which causes a problem that the apparatus is more likely to be enlarged.

According to the present invention, an image pickup unit with a structure contributable to reduction in size of an apparatus while maintaining performance and an endoscope to which the image pickup unit is applied can be provided.

Further, according to the present invention, an image pickup unit with a structure capable of achieving expansion of a mounting area of a circuit board and addressing enhanced functionality while restricting enlargement of an apparatus with the outer size maintained, and an endoscope to which the image pickup unit is applied can be provided.

Hereinafter, the present invention is described by way of an illustrated embodiment.

The drawings used in the following description are schematic illustrations, and in some cases, the dimensional relation, the scale, and the like of the members are shown differently for each constituent element in order for each constituent element to be shown in a size perceivable on the drawings. Therefore, in the present invention, the quantity, the shape, the ratio in size, the relative positional relation, and the like of the constituent elements illustrated in the drawings are not limited to the examples shown in the drawings.

First, before describing a detailed configuration of an image pickup unit of an embodiment of the present invention, an overall schematic configuration of an endoscope system including an endoscope to which the image pickup unit of the present embodiment is applied is briefly described below with reference to FIG. 1.

FIG. 1 is an outer appearance view showing the endoscope system including the endoscope to which the image pickup unit of the embodiment of the present invention is applied. A basic configuration of the endoscope system is substantially the same as a configuration of the conventional endoscope system. Therefore, in the following description, the constituent members of the endoscope system are only schematically described.

As shown in FIG. 1, an endoscope system 1 including the endoscope to which the image pickup unit of the present embodiment is applied is mainly configured with an endoscope 2, a light source device 3, a video processor 4, a display device 5, and the like.

As shown in FIG. 1, the endoscope 2 is mainly configured with an insertion portion 9 in a substantially elongated tubular shape, an operation portion 10 in a substantially box shape where the insertion portion 9 is provided so as to extend, a universal cord 12, and the like.

The insertion portion 9 of the endoscope 2 is configured with a distal end portion 6, a bending portion 7, and a flexible tube portion 8 that are continuously provided in order from a distal end side. A proximal end portion of the insertion portion 9 is connected to the operation portion 10.

An image pickup unit 20 of the present embodiment is disposed inside the distal end portion 6. A detailed configuration of the image pickup unit 20 of the present embodiment is described later (see FIG. 2 to FIG. 10).

The operation portion 10 is mainly configured with a forceps port 11 including an opening for allowing insertion of a treatment instrument or the like, an operation portion main body constituting a grasping portion, a plurality of operating members that are provided on an outer surface of the operation portion main body and that perform various operations of the endoscope 2, and the like.

The forceps port 11 provided in the operation portion 10 constitutes an opening portion on a proximal end side of a treatment instrument channel (not shown) disposed by insertion from the operation portion 10 through an opening portion on a distal end side of the distal end portion 6 of the insertion portion 9.

The universal cord 12 is a tubular member extending from a lateral side of the operation portion 10. A distal end site of the universal cord 12 is provided with a scope connector 13. The scope connector 13 is connected to the light source device 3.

The light source device 3 is a device that supplies illumination light to a lighting device (not shown) provided inside the distal end portion 6 of the insertion portion 9 of the endoscope 2. The illumination light emitted from the light source device 3 is transmitted, to the distal end portion 6 of the insertion portion 9 of the endoscope 2, by passing through an optical fiber cable (not shown) disposed by insertion from the scope connector 13, the universal cord 12, and the operation portion 10 through the insertion portion 9. The illumination light then transmits through a lighting optical member provided on a front surface of the distal end portion 6 and is radiated toward an observation target on a front side of the distal end portion 6.

A scope cable 14 laterally extends from the scope connector 13. A distal end site of the scope cable 14 is provided with an electric connector portion 15. The electric connector portion 15 is connected to the video processor 4.

The video processor 4 is a control device that controls the overall present endoscope system 1. In this case, the video processor 4 includes a signal processing circuit that receives an image pickup signal from the image pickup unit 20 provided inside the distal end portion 6 of the insertion portion 9 of the endoscope 2 and performs predetermined signal processing, a control processing circuit that outputs a control signal or the like to drive the image pickup unit 20, and the like.

The video processor 4 and the image pickup unit 20 are electrically interconnected by means of a signal transmission cable (hereinafter, simply referred to as a cable) 60. Therefore, the cable 60 is disposed by insertion from the electric connector portion 15, the universal cord 12, and the operation portion 10 through the distal end portion 6 of the insertion portion 9. With this configuration, the image pickup signal outputted from the image pickup unit 20, the control signal outputted from the video processor 4, and the like are transmitted between the image pickup unit 20 and the video processor 4 via the cable 60. Note that as a form of the cable 60, a composite cable, or the like, in the form of a bundle of a plurality of cables covered with a sheath shield, a sheath tube, or the like is adopted.

The video processor 4 and the display device 5 are interconnected using a video cable 16. The video cable 16 transmits, to the display device 5, the image signal, the control signal, and the like outputted from the video processor 4.

The display device 5 receives the image signal or the control signal outputted from the video processor 4, and displays an endoscope image in a predetermined form and various information in a display mode in accordance with the received control signal. The endoscope system 1, which includes the endoscope 2 to which the image pickup unit 20 of the present embodiment is applied, is generally configured as described above. Note that the other configurations of the endoscope system 1 are substantially the same as the configurations of the conventional endoscope system of the same type.

Figure 2:
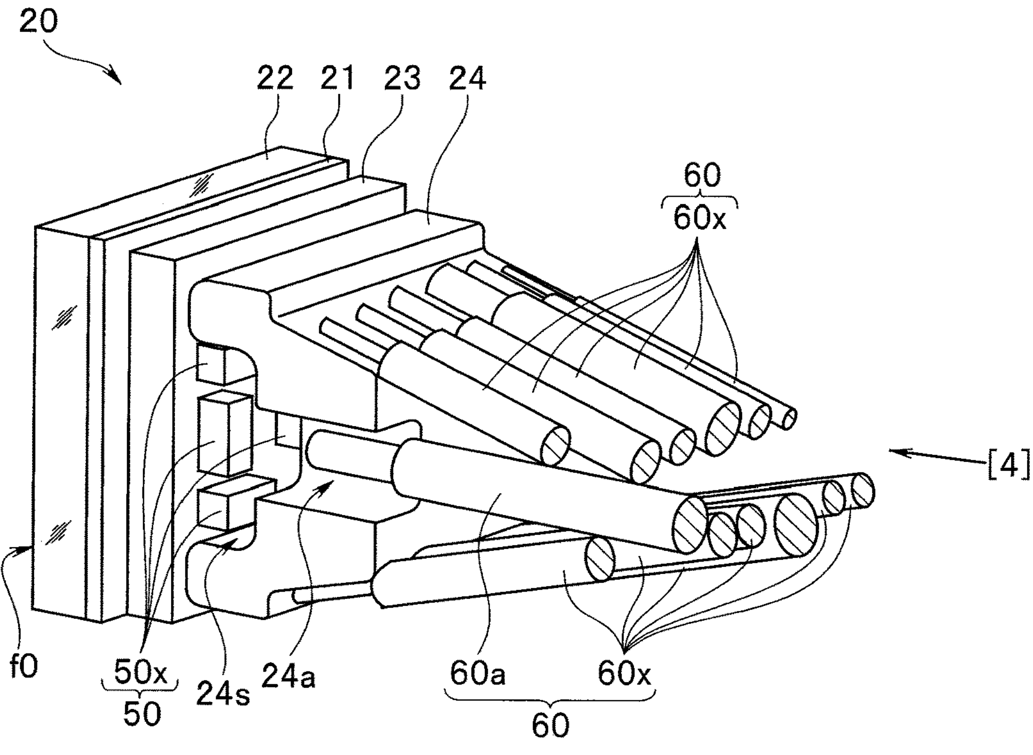
FIG. 2 is an outer appearance perspective view of a right side surface of the image pickup unit of the embodiment of the present invention when viewed from a position obliquely rearward on the right.
Figure 3:
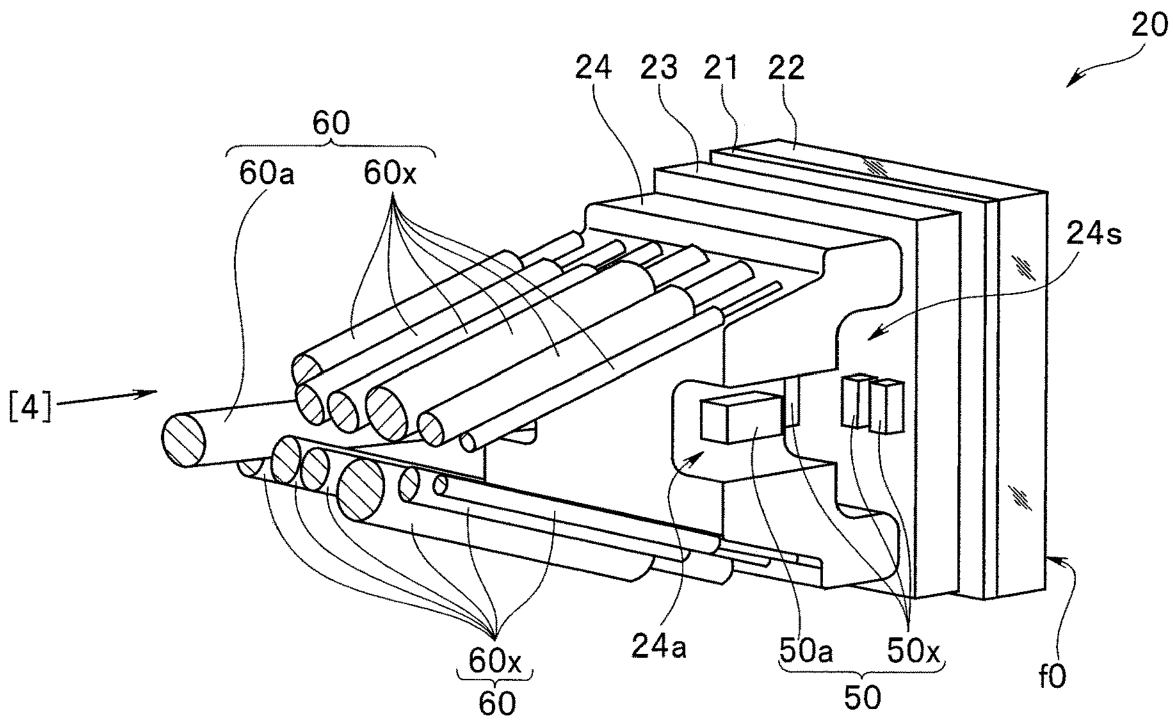
FIG. 3 is an outer appearance perspective view of a left side surface of the image pickup unit of the embodiment of the present invention when viewed from a position obliquely rearward on the left.

Next, the configuration of the image pickup unit of the present embodiment is described below in detail with reference to FIG. 2 to FIG. 10. FIG. 2 and FIG. 3 are perspective views showing an outer appearance of the image pickup unit of the present embodiment. Here, reference numeral f shown in FIG. 2 and FIG. 3 indicates a front surface region of the image pickup unit. When the following description indicates the left and the right, the left and the right as viewed from a position facing the front surface region f0 of the image pickup unit 20 are referred to, unless otherwise specified.

Figure 4:
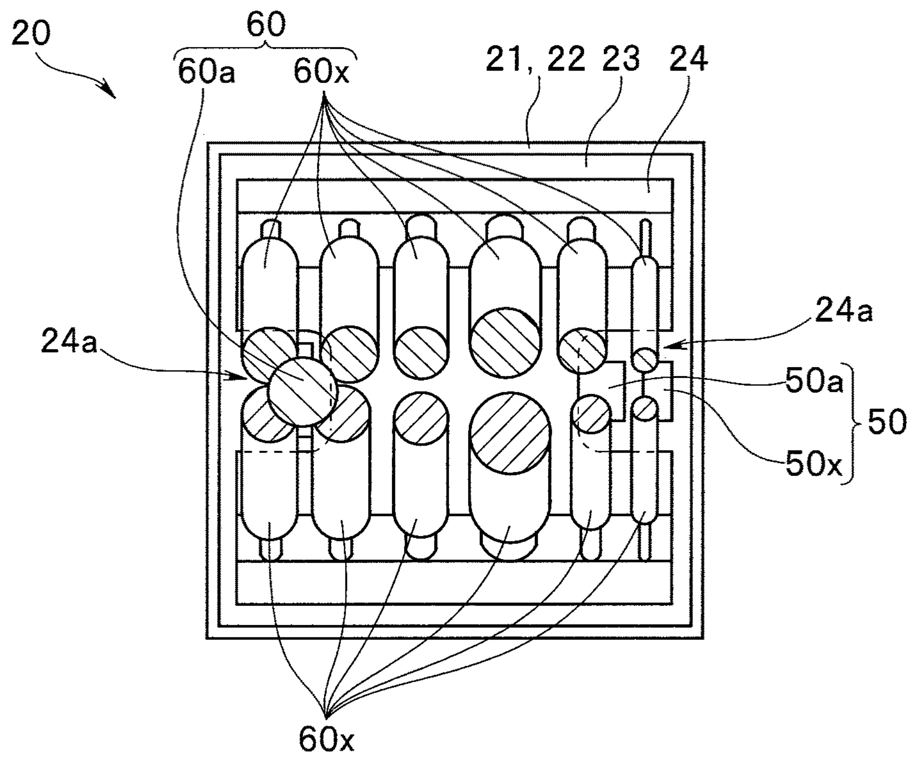
FIG. 4 is a plan view of the image pickup unit of the embodiment of the present invention when viewed from a back surface side.
Figure 5:
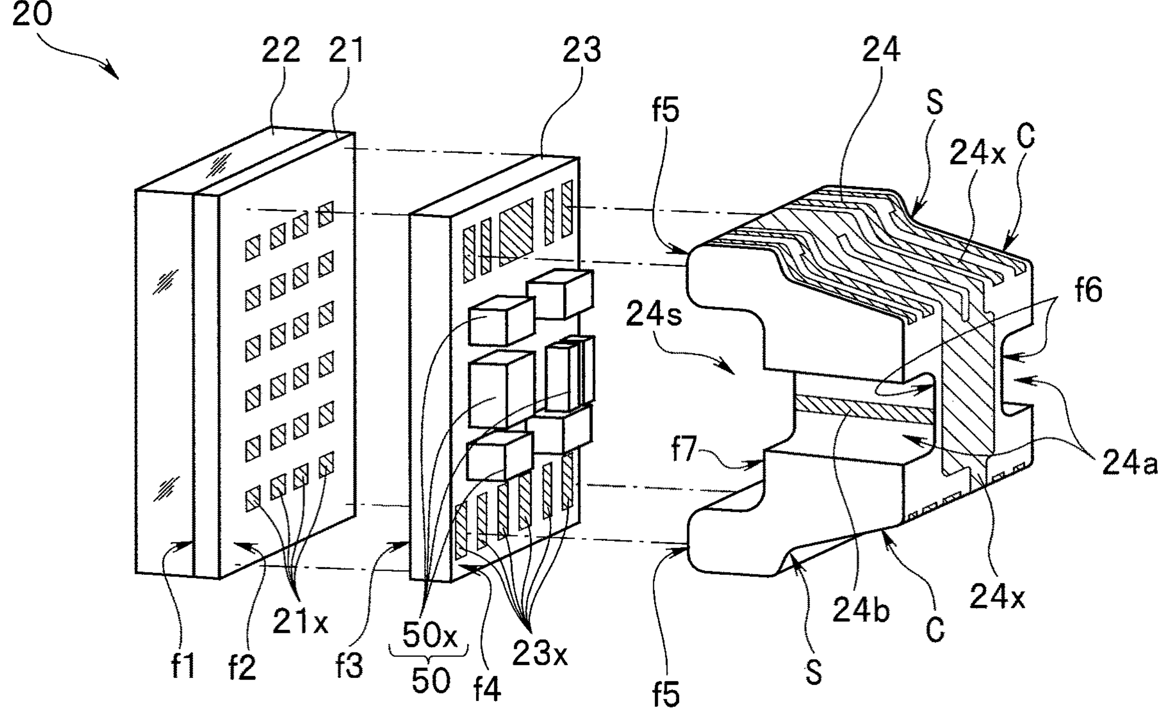
FIG. 5 is an exploded perspective view showing the image pickup unit of the embodiment of the present invention as exploded.

FIG. 2 is a perspective view of a right side surface of the image pickup unit of the present embodiment when viewed from a position obliquely rearward on the right. FIG. 3 is a perspective view of a left side surface of the image pickup unit of the present embodiment when viewed from a position obliquely rearward on the left. FIG. 4 is a plan view of the image pickup unit of the present embodiment when viewed from a back surface side (direction of an arrow [4] of FIG. 2 and FIG. 3). FIG. 5 is an exploded perspective view showing the image pickup unit of the present embodiment as exploded. Note that in FIG. 5, to avoid complexity of the drawing, only the main constituent members are illustrated in a simplified manner, omitting some constituent members (mainly cables).

Figure 6:
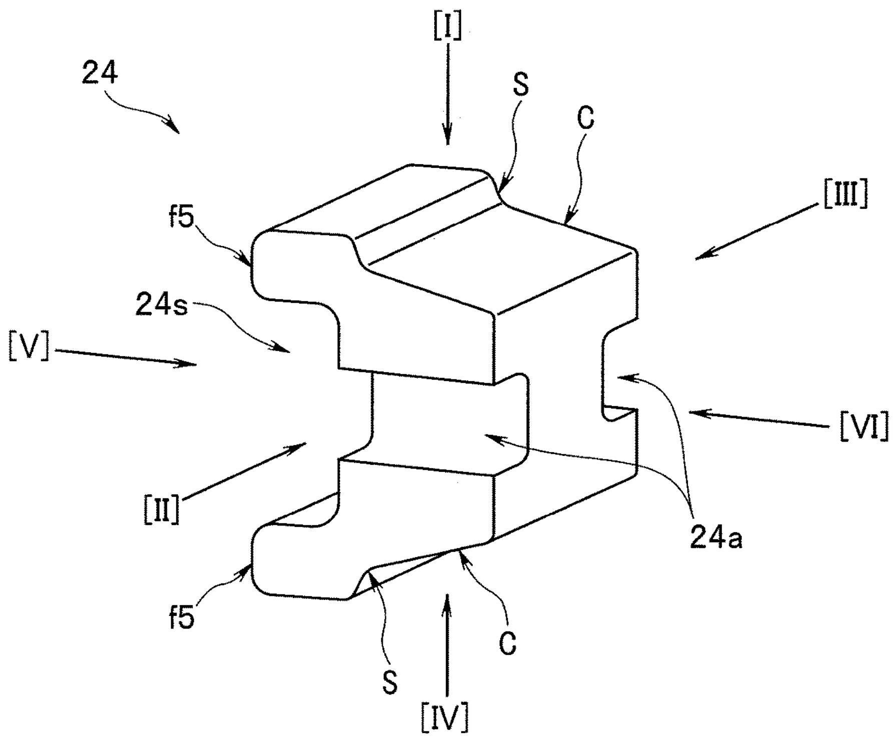
FIG. 6 is a perspective view of a three-dimensional circuit board in the image pickup unit of the embodiment of the present invention when viewed from an obliquely rear side on the right.
Figure 7:
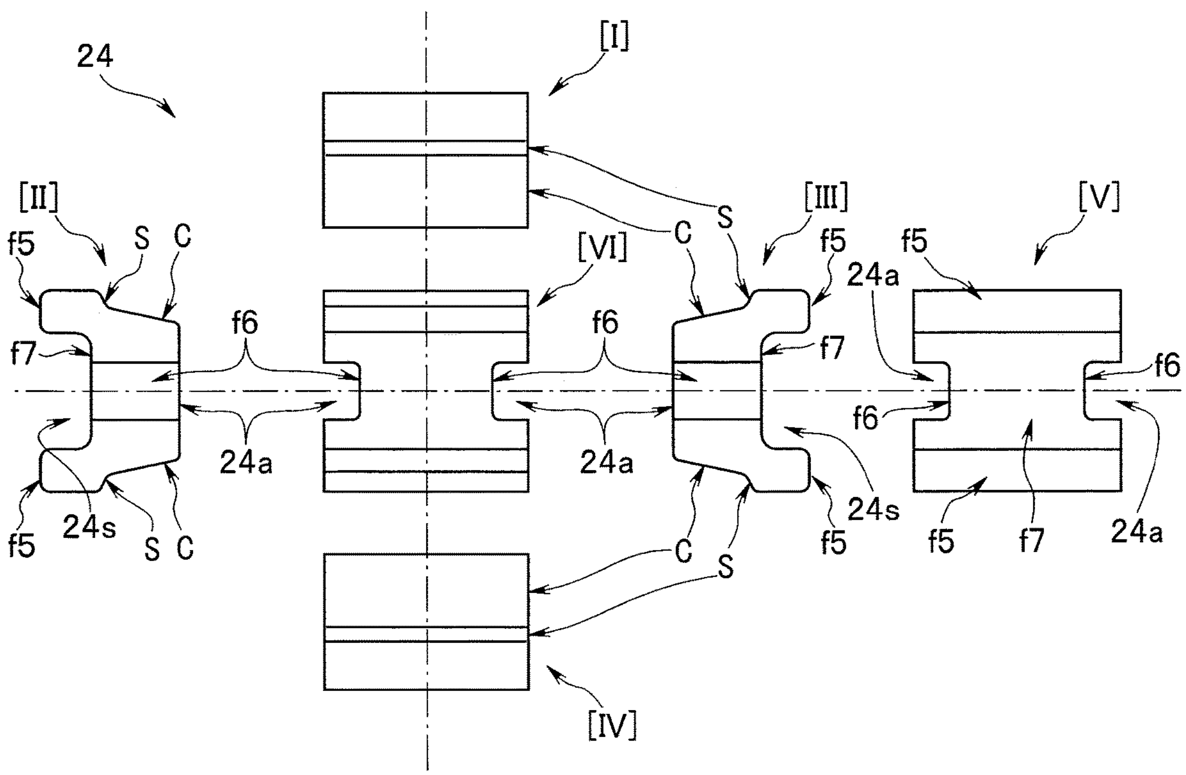
FIG. 7 is a view of six sides of the three-dimensional circuit board in the image pickup unit of the embodiment of the present invention.

FIG. 6 to FIG. 9 are views showing a three-dimensional circuit board, which is extracted alone, in the image pickup unit of the present embodiment. Of the drawings, FIG. 6 and FIG. 7 are views presented to define a name of each surface of the three-dimensional circuit board. Here, FIG. 6 is a perspective view of the three-dimensional circuit board when viewed from an obliquely rear side on the right. FIG. 7 is a view of six sides of the three-dimensional circuit board.

Figure 8:
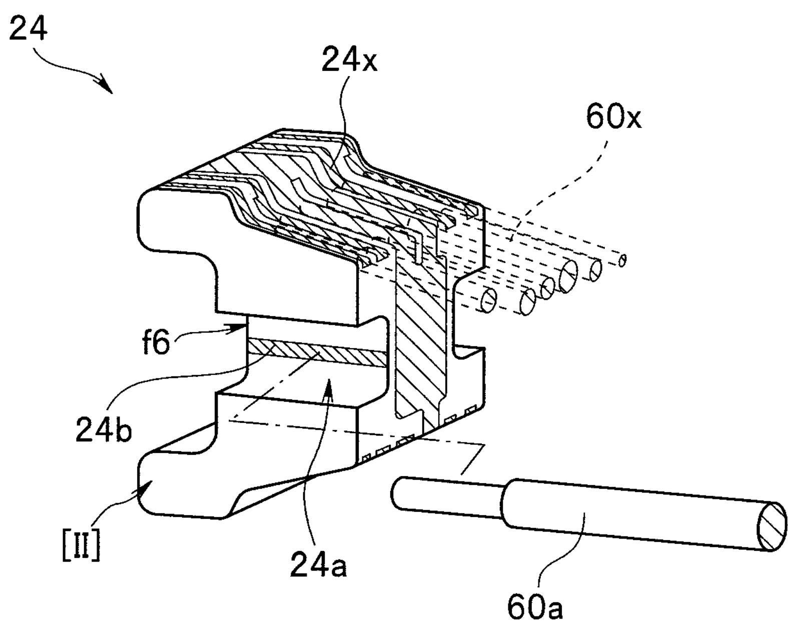
FIG. 8 is a perspective view of mainly a right side surface of the three-dimensional circuit board in the image pickup unit of the embodiment of the present invention when viewed from the obliquely rear side on the right, showing a connecting site where a cable is connected to the three-dimensional circuit board.
Figure 9:
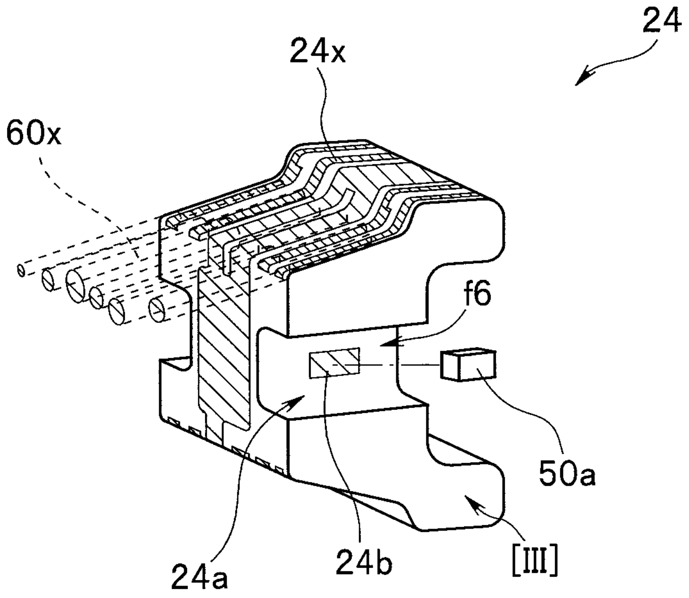
FIG. 9 is a perspective view of mainly a left side surface of the three-dimensional circuit board in the image pickup unit of the embodiment of the present invention when viewed from an obliquely rear side on the left, showing a connecting site where an electronic component is mounted on the three-dimensional circuit board.
Figure 10:
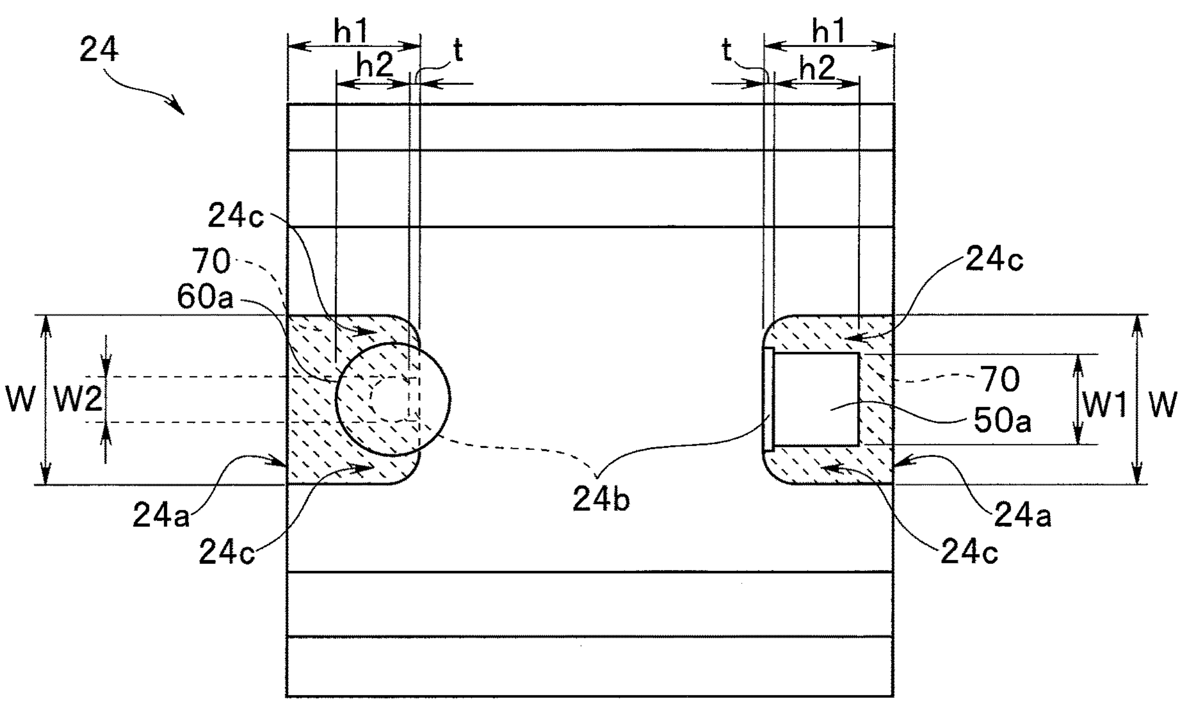
FIG. 10 is a plan view of the three-dimensional circuit board in the image pickup unit of the embodiment of the present invention when viewed from a back surface side, showing a state in which a cable connecting site and an electronic component mounting site are sealed with resin.

FIG. 8, FIG. 9, and FIG. 10 show the connecting relation between the three-dimensional circuit board in the image pickup unit of the present embodiment and a cable (FIG. 8 and FIG. 10) connected to or an electronic component (FIG. 9 and FIG. 10) mounted on the three-dimensional circuit board. Of the drawings, FIG. 8 is a perspective view of mainly a right side surface of the three-dimensional circuit board when viewed from the obliquely rear side on the right. FIG. 8 shows the connecting relation between the three-dimensional circuit board and the cable. FIG. 9 is a perspective view of mainly a left side surface of the three-dimensional circuit board when viewed from an obliquely rear side on the left. FIG. 9 shows the connecting relation between the three-dimensional circuit board and the electronic component. FIG. 10 is a plan view of the three-dimensional circuit board when viewed from a back surface side. Note that in FIG. 8 to FIG. 10, to avoid complexity of the drawings and to clarify the connecting relation between the three-dimensional circuit board and the electronic component mounted on or the cable connected to the three-dimensional circuit board, illustration of the constituent members other than the three-dimensional circuit board and the electronic component mounted on or the cable connected to the three-dimensional circuit board is omitted.

As shown in FIG. 2 to FIG. 5 or the like, the image pickup unit 20 is mainly configured with an image pickup device 21, a cover glass 22, a flat circuit board 23, a three-dimensional circuit board 24, a plurality of electronic components 50 (50*x*, 50*a*) mounted on and a plurality of cables 60 (60*x*, 60*a*) connected to each circuit board (23, 24), and the like.

The image pickup device 21 is an electronic component that receives light of an optical image of an observation target, the image of which is formed by an image-forming optical lens unit (not shown), and that performs predetermined photoelectric conversion processing to generate an image signal. As the image pickup device 21, an image sensor in a typical form, such as a CCD (charge coupled device) or a CMOS (complementary metal oxide semiconductor), or the like is adopted.

The cover glass 22, which is a protective glass, is provided on a front surface of the image pickup device 21, that is, a light receiving surface (region depicted by reference numeral f1 of FIG. 5) side. In a state in which the image pickup unit 20 is disposed inside the distal end portion 6 of the endoscope 2, the image-forming optical lens unit (not shown) is disposed on a front side of the image pickup device 21. In this case, the image-forming optical lens unit is disposed such that an optical axis (not shown) substantially corresponds with a substantially center axis of the image pickup device 21. The light receiving surface (region f1) of the image pickup device 21 is disposed parallel to a plane orthogonal to the optical axis (not shown) of the image-forming optical lens unit. With this configuration, the light from the observation target that is condensed by the image-forming optical lens unit is made incident from the front surface region f0 of the cover glass 22 and passes through the cover glass 22, and an image is formed on the light receiving surface (region f1) of the image pickup device 21.

As shown in FIG. 5, bumps (not shown) formed of a plurality of connection lands 21*x*, solder, and the like are formed in a region (surface depicted by reference numeral f2 of FIG. 5) on a back surface side of the image pickup device 21. The bumps formed of the plurality of connection lands 21*x*, the solder, and the like are connected to a plurality of connection electrodes (not shown) formed on a front surface region (surface depicted by reference numeral f3 of FIG. 5) side of the flat circuit board 23. With this configuration, the image pickup device 21 and the flat circuit board 23 are electrically connected. A connecting portion between the image pickup device 21 and the flat circuit board 23 is sealed with sealing resin (not shown).

Here, for a package including the image pickup device 21 and the cover glass 22, a CSP (chip size package) or the like is adopted, in which the size of an image pickup device chip finally obtained after the image pickup device chip in a wafer state undergoes processes of wiring, electrode forming, resin sealing, dicing, and the like becomes the size of the package.

The flat circuit board 23 is a circuit board provided substantially parallel to the image pickup device 21 and generally formed of a flat plate member. As described above, the flat circuit board 23 and the image pickup device 21 are electrically interconnected. Therefore, a plurality of connection electrodes (not shown) connected to the image pickup device 21 are formed in the front surface region f3 of the flat circuit board 23.

A plurality of connection electrodes 23*x* are formed in a region (surface depicted by reference numeral f4 of FIG. 5) on a back surface side of the flat circuit board 23. A plurality of connection electrodes (not shown) formed in a partial region (region depicted by reference numeral f5 of FIG. 5) on a front surface side of the three-dimensional circuit board 24 are connected to a part of the plurality of connection electrodes 23*x*. The plurality of electronic components 50*x* are mounted on another part of the plurality of connection electrodes 23*x*. The plurality of electronic components 50*x* are passive components, or the like, such as a capacitor, a resistor, and a coil, and active components, such as a transistor, a diode, and a drive IC.

The plurality of electronic components 50*x* are mounted on the connection electrodes 23*x* in a substantially center region on a region f4 side on the back surface side of the flat circuit board 23. The plurality of connection electrodes (not shown) in the partial region f5 on the front surface side of the three-dimensional circuit board 24 are connected to the connection electrodes 23*x* in a peripheral region on the region f4 side on the back surface side of the flat circuit board 23.

The flat circuit board 23 is a multilayer-structure substrate in a form of a plurality of substrates stacked. As the substrates stacked in the flat circuit board 23, a ceramic substrate, an epoxy glass substrate, a flexible substrate, a glass substrate, a silicon substrate, and the like are adopted. Note that since the structure of the flat circuit board 23 itself is the same as the structure conventionally, typically used, the detailed description of the structure is omitted.

The three-dimensional circuit board 24 is a circuit board in a three-dimensional structure. For the three-dimensional circuit board 24, a MID (molded interconnect device) substrate, or the like, in the form in which a three-dimensional wiring is formed by injection molding is adopted. As the three-dimensional circuit board 24, a ceramic substrate, an epoxy glass substrate, a glass substrate, a silicon substrate, or the like, other than the MID substrate, may also be adopted.

The three-dimensional circuit board 24 is formed with a plurality of outwardly facing surfaces (hereinafter, referred to as outer surfaces). Here, the plurality of outer surfaces of the three-dimensional circuit board 24 are defined as follows with reference to FIG. 6 and FIG. 7.

As described above, FIG. 6 is a perspective view of a right side surface of the three-dimensional circuit board 24 when viewed from an obliquely rear side on the right. FIG. 7 is a view of six sides of the three-dimensional circuit board 24. In this case, reference numeral [I] shown in FIG. 6 indicates an upper surface of the three-dimensional circuit board 24. Reference numeral [II] shown in FIG. 6 indicates the right side surface of the three-dimensional circuit board 24. Reference numeral [III] shown in FIG. 6 indicates a left side surface of the three-dimensional circuit board 24. Reference numeral [IV] shown in FIG. 6 indicates a lower surface of the three-dimensional circuit board 24. Reference numeral [V] shown in FIG. 6 indicates a front surface of the three-dimensional circuit board 24. Reference numeral [VI] shown in FIG. 6 indicates a back surface of the three-dimensional circuit board 24.

Further, reference numeral [1] shown in FIG. 7 corresponds to an upper surface view of the three-dimensional circuit board 24. Reference numeral [II] shown in FIG. 7 corresponds to a right side surface view of the three-dimensional circuit board 24. Reference numeral [III] shown in FIG. 7 corresponds to a left side surface view of the three-dimensional circuit board 24. Reference numeral [IV] shown in FIG. 7 corresponds to a lower surface view of the three-dimensional circuit board 24. Reference numeral [V] shown in FIG. 7 corresponds to a front surface view of the three-dimensional circuit board 24. Reference numeral [VI] shown in FIG. 7 corresponds to a back surface view of the three-dimensional circuit board 24.

In the following description, the surface depicted by reference numeral [I] of FIG. 6 and FIG. 7 is defined as a first surface [I] of the three-dimensional circuit board 24. The surface depicted by reference numeral [II] of FIG. 6 and FIG. 7 is defined as a second surface [II] of the three-dimensional circuit board 24, which is a surface substantially orthogonal to the first surface [I]. The surface depicted by reference numeral [III] of FIG. 6 and FIG. 7 is defined as a third surface [III] of the three-dimensional circuit board 24, which is a surface facing opposite to the second surface [II]. The surface depicted by reference numeral [IV] of FIG. 6 and FIG. 7 is defined as a fourth surface [IV] of the three-dimensional circuit board 24, which is a surface facing opposite to the first surface [I]. The surface depicted by reference numeral [V] of FIG. 6 and FIG. 7 is defined as a fifth surface [V] of the three-dimensional circuit board 24, which is a front surface of the three-dimensional circuit board 24, that is, a surface facing a region f4 on the back surface side of the flat circuit board 23 when the three-dimensional circuit board 24 is assembled as the image pickup unit 20. The surface depicted by reference numeral [VI] of FIG. 6 and FIG. 7 is defined as a sixth surface [VI] of the three-dimensional circuit board 24, which is a back surface of the three-dimensional circuit board 24. That is, the sixth surface [VI] is a surface facing opposite to the fifth surface [V].

In this case, a step portion S and an inclined portion C are formed on the first surface [I] and the fourth surface [IV] (see FIG. 5 to FIG. 7) of the outer surfaces of the three-dimensional circuit board 24. The step portion S is formed in a site closer to the front surface of the three-dimensional circuit board 24 and has at least one step toward the center axis of the three-dimensional circuit board 24 from each surface ([I], [IV]).

The inclined portion C is an inclined surface formed so as to extend from a proximal end of the step portion S on each surface ([I], [IV]) toward the back surface side in a direction (an optical axis direction of the image-forming optical lens unit that is not shown) substantially orthogonal to the light receiving surface (region f1) of the image pickup device 21 and to extend in a direction (a direction toward the center axis) in which the inclined portions C of the respective surfaces approach to each other. Note that a surface continuously formed with the step portion S may be parallel to the optical axis direction of the image-forming optical lens unit.

A plurality of connection electrodes 24*x* in a predetermined form are formed on the first surface [I], the fourth surface [IV], and the sixth surface [VI] of the outer surfaces of the three-dimensional circuit board 24 (see FIG. 5, FIG. 8, and FIG. 9). Note that in FIG. 2 to FIG. 4, FIG. 6, and FIG. 7, illustration of the plurality of connection electrodes 24*x* is omitted.

Core wires of the plurality of cables 60*x* are respectively connected, by solder connection or the like, to the plurality of connection electrodes 24*x* formed in a region of each inclined portion C of the first surface [I] and the fourth surface [IV].

At this time, as described above, since the step portion S and the inclined portion C are provided on each surface of the first surface [I] and the fourth surface [IV], the plurality of cables 60*x* connected to the connection electrodes 24*x* in each inclined portion C are arranged in such a form as being fitted within a projection plane in the optical axis direction of the image pickup unit 20 when the front surface of the image pickup unit 20 is viewed from a position facing the front surface side of the image pickup unit 20.

The plurality of connection electrodes 24*x* are connected to the connection electrodes (not shown) in the partial region f5 of the fifth surface [V]. When the three-dimensional circuit board 24 is assembled in the image pickup unit 20, the connection electrodes (not shown) in the partial region f5 of the fifth surface [V] are connected to the plurality of connection electrodes 23*x* on the back surface side of the flat circuit board 23. In this manner, the plurality of connection electrodes 24*x* of the three-dimensional circuit board 24 are connected to the connection electrodes 23*x* of the flat circuit board 23.

As described above, the plurality of cables 60*x* are connected, by solder connection or the like, to the plurality of connection electrodes 24*x* of the three-dimensional circuit board 24 (see FIG. 2 to FIG. 4, FIG. 8, and FIG. 9). In this manner, the electrical connection between the image pickup unit 20 and the video processor 4 is secured via the image pickup device 21, the flat circuit board 23, the three-dimensional circuit board 24, and the cable 60.

A recessed portion 24*s* for component avoidance is formed on the fifth surface [V] of the outer surfaces of the three-dimensional circuit board 24. The recessed portion 24*s* for component avoidance is formed in a groove shape, for example, which is inserted from the second surface [II] through the third surface [III] in a substantially center portion of the fifth surface [V]. The recessed portion 24*s* for component avoidance is a site having functions of avoiding interference between the plurality of electronic components 50*x* mounted on the back surface of the flat circuit board 23 and the three-dimensional circuit board 24 and simultaneously covering the outer surface of the plurality of electronic components 50*x* so as to house the plurality of electronic components 50*x* inside the recessed portion 24*s* for component avoidance, when the three-dimensional circuit board 24 is assembled as the image pickup unit 20 (see FIG. 2, FIG. 3, and FIG. 5). Therefore, the connection electrodes are not formed in a groove bottom region f7 of the recessed portion 24*s* for component avoidance of the fifth surface [V]. Note that in a state of the image pickup unit 20 being assembled, the inside of the recessed portion 24*s* for component avoidance is sealed with sealing resin.

A recessed portion 24*a* for component mounting is formed on each of the second surface [II] and the third surface [III] of the outer surfaces of the three-dimensional circuit board 24. The recessed portions 24*a* for component mounting are each formed in a groove shape, for example, which is inserted from the fifth surface [V] through the sixth surface [VI] in a substantially center portion of each surface of the second surface [II] and the third surface [III]. The recessed portions 24*a* for component mounting are sites where a predetermined cable 60*a* (see FIG. 8) is connected or a predetermined electronic component 50*a* (see FIG. 9) is mounted when the three-dimensional circuit board 24 is assembled as the image pickup unit 20. Therefore, a connection terminal portion 24*b* (see FIG. 5 and FIG. 8) is formed in a groove bottom region f6 of each recessed portion 24*a* for component mounting.

In this case, the cable 60*a* (see FIG. 8) connected to the recessed portion 24*a* for component mounting is housed in the recessed portion 24*a* for component mounting in such a form as not externally (laterally) projecting from the second surface [II] or the third surface [III] (the second surface [II] in the present embodiment). The electronic component 50*a* (see FIG. 9) mounted in the recessed portion 24*a* for component mounting is housed in the recessed portion 24*a* for component mounting in such a form as not externally (laterally and toward the back surface side) projecting from the second surface [II] or the third surface [III] (the third surface [III] in the present embodiment) and the sixth surface [VI].

For example, in FIG. 10, reference numeral h1 is assumed to be a depth dimension of the recessed portion for component mounting, reference numeral h2 is assumed to be a projecting dimension of the cable or the electronic component, and reference numeral t is assumed to be a thickness dimension of the connection terminal portion. Here, when the cable 60*a* is connected to the connection terminal portion 24*b* in the recessed portion 24*a* for component mounting, a core wire portion of the cable 60*a* is actually connected by soldering to the connection terminal portion 24*b*. In this case, a sheath portion (major diameter portion) of the cable 60*a* is in such a form as projecting toward an external back surface of the sixth surface [VI](see FIG. 2). Therefore, when the cable 60*a* is disposed by connection in the recessed portion 24*a* for component mounting, actually, a part of the cable 60*a* is housed within the recessed portion 24*a* for component mounting, which corresponds to, for example, the core diameter+sheath thickness of the cable 60*a*, as shown in FIG. 10. The core diameter+sheath thickness of the cable 60*a* corresponds to the projecting dimension of the cable 60*a*. When the electronic component 50*a* is mounted on the connection terminal portion 24*b* in the recessed portion 24*a* for component mounting, the height dimension of the electronic component 50*a* exactly corresponds to the projecting dimension of the electronic component 50*a*.

In this case, each value (h1, h2, t) is set so as to satisfy $h1 \geq h2 + t$. In other words, when $h1 \geq h2 + t$ is satisfied, the cable 60*a* or the electronic component 50*a* housed in the recessed portion 24*a* for component mounting does not externally project from the second surface [II] or the third surface [III].

At this time, a gap 24*c* is provided in a portion where an outer surface of the electronic component 50*a* or the cable 60*a* housed in the recessed portion 24*a* for component mounting and an inner wall surface of each recessed portion 24*a* for component mounting face each other. Therefore, a groove width W of the recessed portion 24*a* for component mounting is set larger than a width dimension W1 of the electronic component 50*a* or a diameter dimension W2 of the core wire of the cable 60*a*. In other words, the groove width W is set so as to satisfy $W > W1$ and $W > W2$.

In such a state, a connecting portion between the connection terminal portion 24*b* in the recessed portion 24*a* for component mounting and (a core wire of) the cable 60*a*, and a connecting portion between the connection terminal portion 24*b* in the recessed portion 24*a* for component mounting and the electronic component 50*a* are sealed with sealing resin 70 filled in the recessed portion 24*a* for component mounting as shown in FIG. 10. At this time, since the gap 24*c* is provided, the sealing resin 70 enters and fills the gap 24*c*.

In such a manner, the configuration is made such that the gap 24*c* is filled with the sealing resin 70 to seal the connecting portion between the three-dimensional circuit board 24 and the electronic component 50*a* or the cable 60*a*, so that the connecting portion is reinforced.

The electronic components 50 (50*x*, 50*a*) mounted on the flat circuit board 23 and the three-dimensional circuit board 24 constitute a signal processing circuit that performs pre-processing and the like of an output signal of the image pickup unit 20, a drive processing circuit that receives a drive signal or the like transmitted from the video processor 4 and drives the image pickup unit 20, and so on. The cables 60 (60*x*, 60*a*) connected to the three-dimensional circuit board 24 function as a signal transmitting member that connects the image pickup unit 20 and the video processor 4.

Of the constituent members of the image pickup unit 20 of the present embodiment configured as such, the flat circuit board 23, the three-dimensional circuit board 24, the plurality of electronic components 50 (50*x*, 50*a*), and the plurality of cables 60 (60*x*, 60*a*) are all set in a size that fits within the projection plane in the optical axis direction of the image pickup unit 20.

As described above, according to the aforementioned embodiment, in the three-dimensional circuit board 24 that is applied to the image pickup unit 20 provided inside the distal end portion 6 of the insertion portion 9 of the endoscope 2, on a part (the second surface III and the third surface [III] in the present embodiment) of the outer surfaces, the recessed portion 24*a* for component mounting in a groove shape that is inserted from the fifth surface [V] through the sixth surface [VI] is formed. The connection terminal portion 24*b* for connection or mounting of the cable 60*a* or the electronic component 50*a* is formed in the groove bottom region f6 of the recessed portion 24*a* for component mounting. After the cable 60*a* or the electronic component 50*a* is connected to or mounted on the connection terminal portion 24*b*, each connecting portion is filled with sealing resin to be sealed. In this case, the cable 60*a* or the electronic component 50*a* housed in the recessed portion 24*a* for component mounting is housed in such a form as not projecting to the outside of each predetermined surface ([II], [III], or [VI]) from the recessed portion 24*a* for component mounting.

By adopting the three-dimensional circuit board 24 configured as such, with the state in which the cable 60*a* and the electronic component 50*a* are housed in the recessed portion 24*a* for component mounting, the three-dimensional circuit board 24 and the cable 60*a* are connected so that the electronic component 50*a* can be mounted on the three-dimensional circuit board 24. In this case, since the recessed portion 24*a* for component mounting is formed in a site having a relatively large area of the second surface [II] and the third surface [III], a larger mounting area can be secured. Further, in this case, since the recessed portion 24*a* for component mounting is formed in a groove shape that is inserted from the fifth surface [V] through the sixth surface [VI] (in the optical axis direction), particularly when the cable 60*a* disposed so as to extend in the optical axis direction is housed in the recessed portion 24*a* for component mounting, the cable 60*a* can be fitted within the projection plane in the optical axis direction of the image pickup unit 20. Simultaneously, externally projecting of the electronic component 50*a* housed in the recessed portion 24*a* for component mounting can also be restricted. Therefore, external enlargement of the image pickup unit 20 around the optical axis can be restricted. By adopting the image pickup unit 20, enlargement in diameter of the endoscope can be restricted.

In other words, according to the present embodiment, for example, since with the recessed portion 24*a* for component mounting provided, the mounting area of the three-dimensional circuit board 24 can be expanded, it is possible to contribute to downsizing the image pickup unit 20 while maintaining the performance. In other words, when the flat circuit board 23 or the three-dimensional circuit board 24 is downsized for downsizing the image pickup unit 20 while maintaining the performance, some electronic components cannot be mounted on or some cables cannot be connected to the downsized flat circuit board 23 or three-dimensional circuit board 24, but according to the configuration of the present embodiment, such electronic components or cables are housed in the recessed portion 24*a* for component mounting of the three-dimensional circuit board 24 so that mounting or connection can be achieved. In this manner, it is possible to contribute to downsizing of the image pickup unit 20 while maintaining the performance of the image pickup unit 20.

According to the configuration of the present embodiment, by adopting the three-dimensional circuit board 24 provided with the recessed portion 24*a* for component mounting, the mounting area can be expanded while maintaining the size of the image pickup unit 20, so that more cables and electronic components can be mounted on the surface of the three-dimensional circuit board 24. Therefore, while maintaining the size of the image pickup unit 20 or restricting the enlargement (thickened diameter in the outer diameter direction or increased length of the outer shape in the longitudinal direction) of the image pickup unit 20, the increase in the number of electronic components mounted on and cables connected to the three-dimensional circuit board 24 can be addressed, thereby contributing to the enhanced functionality of the image pickup unit 20.

Further, the groove width W of the recessed portion 24*a* for component mounting is appropriately set so as to fit the width dimensions (diameter dimensions) W1, W2 of the electronic component 50*a* and the cable 60*a* that are housed in the recessed portion 24*a* for component mounting, so that the gap 24*c* with a predetermined distance is provided between the recessed portion 24*a* for component mounting and the electronic component 50*a* and the cable 60*a* housed in the recessed portion 24*a* for component mounting. The gap 24*c* has a predetermined distance that is enough for the gap 24*c* to be filled with the sealing resin 70. Therefore, by filling the gap 24*c* with the sealing resin 70, the connecting portion between the three-dimensional circuit board 24 and the electronic component 50*a* or the cable 60*a* housed in the recessed portion 24*a* for component mounting can be reinforced.

Note that in the present embodiment, the example of the three-dimensional circuit board 24 in which one recessed portion 24*a* for component mounting is provided for each of the second surface [II] and the third surface [III] has been shown, but the three-dimensional circuit board 24 is not limited to the embodiment. The recessed portions 24*a* for component mounting only need to be provided in the three-dimensional circuit board 24 of the image pickup unit 20 in the only required number, as appropriate, in accordance with the numbers or the like of the electronic components and the cables that are mounted, and the configuration only needs to be made such that at least one of the recessed portions 24*a* for component mounting is provided on either the second surface [II] or the third surface [III].

Further, in the aforementioned embodiment, the example in which the recessed portion 24*a* for component mounting is provided on the second surface [II] or the third surface [III] of the three-dimensional circuit board 24 has been shown, but the position where the recessed portion 24*a* for component mounting is provided is not limited to the illustrated example. Configuration examples of the three-dimensional circuit board with different recessed portions for component mounting are shown below.

[First Modification]

Figure 11:
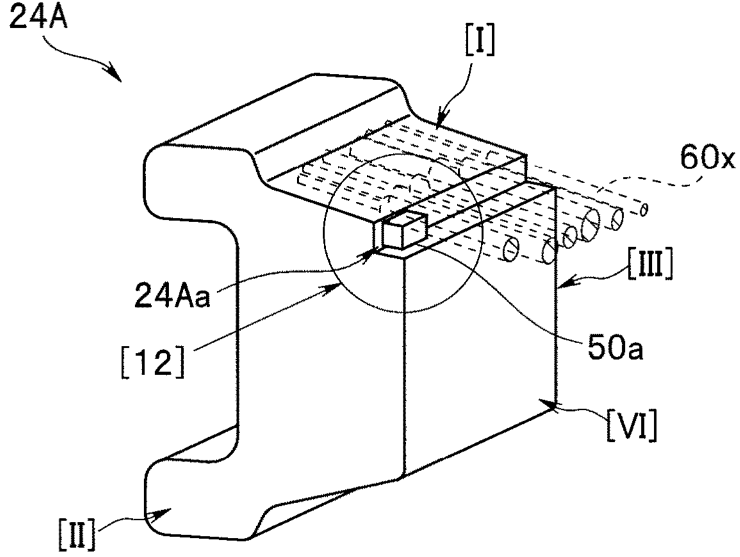
FIG. 11 is a view showing a first modification of the three-dimensional circuit board in the image pickup unit of the embodiment of the present invention, showing an outer shape of the three-dimensional circuit board, which is extracted alone, of the first modification.
Figure 12:
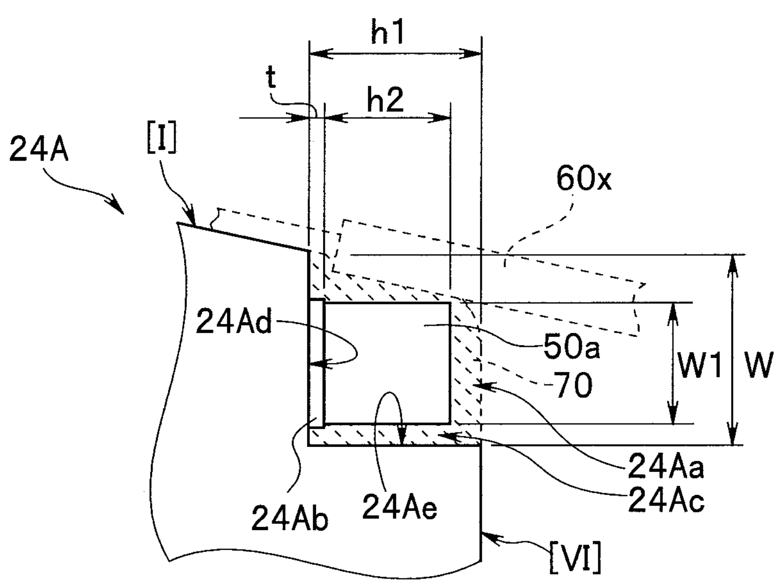
FIG. 12 is a view of an enlarged right side surface of a portion depicted by reference numeral [12] of FIG. 11.

FIG. 11 and FIG. 12 are views showing a first modification of the three-dimensional circuit board in the image pickup unit of the embodiment of the present invention. FIG. 11 shows an outer shape of the three-dimensional circuit board, which is extracted alone, of the first modification. Therefore, in FIG. 11, illustration of the connection electrodes 24*x* formed on the outer surface of the three-dimensional circuit board is omitted. FIG. 12 is a view of an enlarged right side surface of a portion depicted by reference numeral [12] of FIG. 11.

A basic configuration of the first modification is substantially the same as the configuration of the aforementioned embodiment. In the first modification, the arrangement of a recessed portion 24Aa for component mounting of a three-dimensional circuit board 24A is the only difference. Therefore, in the following description, illustration of the same constituent members as the constituent members of the aforementioned embodiment is omitted, and description of the same constituent members is omitted. Only the portions different from the portions of the aforementioned embodiment are described below.

As shown in FIG. 11 and FIG. 12, in the three-dimensional circuit board 24A in the first modification, the recessed portion 24Aa for component mounting is formed in a site where the first surface [I] and the sixth surface [VI] cross each other. In other words, the recessed portion 24Aa for component mounting is in a form in which a portion of each of the first surface [I] and the sixth surface [VI] is cut out.

As shown in FIG. 11, the recessed portion 24Aa for component mounting is formed in a groove shape that is inserted from the second surface [II] through the third surface [III] (in a direction orthogonal to the optical axis). At least one electronic component 50*a* is mounted in the recessed portion 24Aa for component mounting.

The recessed portion 24Aa for component mounting has two surfaces facing an outer surface of the three-dimensional circuit board 24A. The two surfaces of the recessed portion 24Aa for component mounting are a first inner surface 24Ad parallel to the sixth surface [VI] and a second inner surface 24Ae orthogonal to the sixth surface [VI] (see FIG. 12).

On either one of the two surfaces (24Ad, 24Ae) of the recessed portion 24Aa for component mounting, a connection terminal portion 24Ab (not shown in FIG. 11; see FIG. 12) is formed. Here, in the first modification, an example in which the connection terminal portion 24Ab is formed on the first inner surface 24Ad is shown. The electronic component 50*a* is mounted on the connection terminal portion 24Ab. At this time, the electronic component 50*a* is housed in the recessed portion 24Aa for component mounting in such a form as not externally projecting from the first surface [I] and the sixth surface [VI]. In other words, the groove width W of the recessed portion 24Aa for component mounting is set larger than the width dimension W1 of the electronic component 50*a* (W>W1).

With such a state, a gap 24Ac with a predetermined distance is provided between the surface (second inner surface 24Ae) where the connection terminal portion 24Ab is not formed, of the first inner surface 24Ad and the second inner surface 24Ae, and the electronic component 50*a* mounted in the recessed portion 24Aa for component mounting. The gap 24Ac and an outer surface side of the electronic component 50*a* are filled with the sealing resin 70. In this manner, the electronic component 50*a* including the connecting portion is sealed with the sealing resin 70. The other configurations are substantially the same as the configurations of the aforementioned embodiment.

According to the first modification configured as described above, exactly the same effects as the effects of the aforementioned embodiment can be obtained. In the first modification, since the electronic component 50*a* housed in the recessed portion 24Aa for component mounting is in such a form as not externally projecting from the first surface [I], the electronic component 50*a* does not interfere with the plurality of cables 60*x* connected to the first surface [I].

Further, since the electronic component 50*a* is in such a form as not externally projecting from the sixth surface [VI], the flatness of the sixth surface [VI] of the three-dimensional circuit board 24A can be secured. This provides an advantage in the manufacturing process of the image pickup unit in that when the three-dimensional circuit board 24A on which components are already mounted is placed on and connected to a flat circuit board (not shown), it is easier to attract and pick up the sixth surface [VI].

Further, according to the first modification, since the recessed portion 24Aa for component mounting is formed in a groove shape that is inserted from the second surface [II] through the third surface [III] (in the direction orthogonal to the optical axis), the shape is convenient for a case in which a mold is removed in a direction orthogonal to the optical axis when the three-dimensional circuit board 24A is produced through die forming.

Since the recessed portion 24Aa for component mounting includes two surfaces (first inner surface 24Ad, second inner surface 24Ae), and the first inner surface 24Ad as one of the surfaces can be provided with the connection terminal portion for connecting the electronic component 50*a*, and the second inner surface 24Ae as the other can be provided with the gap 24Ac for the sealing resin, the electronic component 50*a* can surely be mounted on the three-dimensional circuit board 24A.

Note that in the first modification, a configuration example in which the recessed portion 24Aa for component mounting is provided in the site where the first surface [I] and the sixth surface [VI] cross each other has been illustrated, but the configuration of the three-dimensional circuit board is not limited to the configuration example. For example, the configuration may be made such that the recessed portion 24Aa for component mounting is provided in a site where the fourth surface [IV] and the sixth surface [VI] cross each other. Such a configuration example can also obtain exactly the same effects as the effects of the first modification.

Further, in the first modification, although a configuration example is made such that the connection terminal portion 24Ab is formed on the first inner surface 24Ad and the gap 24Ac is provided on the second inner surface 24Ae, the configuration of the three-dimensional circuit board is not limited to the configuration example. For example, the configuration may be made such that the gap 24Ac is provided on the first inner surface 24Ad and the connection terminal portion 24Ab is formed on the second inner surface 24Ae. Such a configuration example can also obtain exactly the same effects as the effects of the first modification.

[Second Modification]

Figure 13:
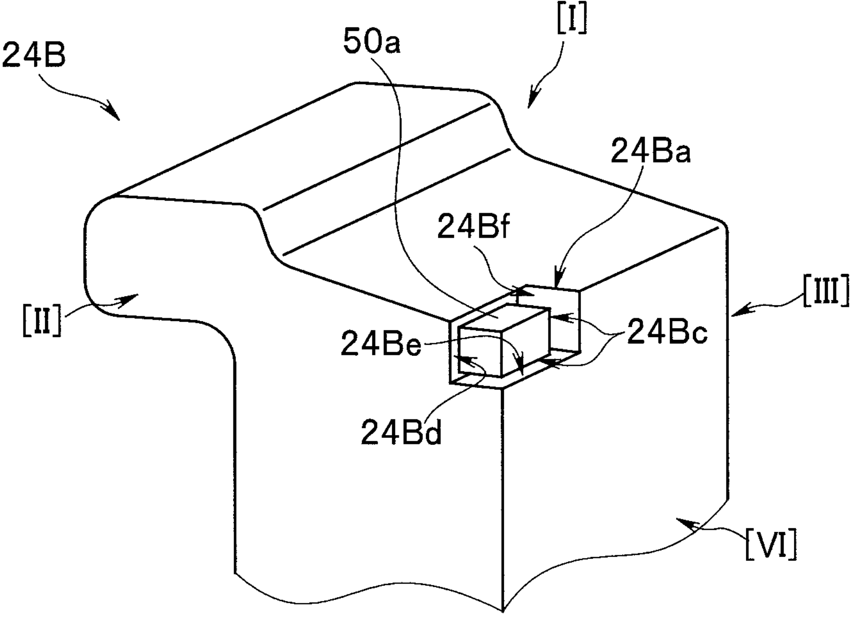
FIG. 13 is a view showing an outer shape of the three-dimensional circuit board, which is extracted alone, of a second modification of the three-dimensional circuit board in the image pickup unit of the embodiment of the present invention.

Next, a second modification of the three-dimensional circuit board in the image pickup unit of the embodiment of the present invention is described with reference to FIG. 13. FIG. 13 illustrates an outer shape of the three-dimensional circuit board, which is extracted alone, of the second modification of the three-dimensional circuit board in the image pickup unit of the embodiment of the present invention. Therefore, in FIG. 13, illustration of the connection electrodes 24*x* formed on the outer surface of the three-dimensional circuit board is omitted.

A basic configuration of the second modification is substantially the same as the configurations of the aforementioned embodiment and first modification. In the second modification, the form of a recessed portion 24Ba for component mounting of a three-dimensional circuit board 24B is the only difference from the first modification. Therefore, in the following description, illustration of the same constituent members as the constituent members of the aforementioned embodiment and first modification is omitted, and description of the same constituent members is omitted. Only the portions different from the portions of the aforementioned embodiment and the first modification are described below.

As shown in FIG. 13, the three-dimensional circuit board 24B in the second modification is similar to the first modification in that the recessed portion 24Ba for component mounting is formed in the site where the first surface [I] and the sixth surface [VI] cross each other. In other words, the recessed portion 24Ba for component mounting is in a form in which a portion of each of the first surface [I] and the sixth surface [VI] is cut out.

However, in the second modification, as shown in FIG. 13, the recessed portion 24Ba for component mounting is formed in a groove shape from the second surface [II] toward the third surface [III] (in the direction orthogonal to the optical axis) and so as to include a wall surface 24Bf parallel to the second surface [11]. At least one electronic component 50*a* is mounted in the recessed portion 24Ba for component mounting.

In the second modification, the recessed portion 24Ba for component mounting includes two surfaces (first inner surface 24Bd, second inner surface 24Be) facing an outer surface of the three-dimensional circuit board 24B, and the wall surface 24Bf.

On either one of the two surfaces (first inner surface 24Bd, second inner surface 24Be) of the recessed portion 24Ba for component mounting, a connection terminal portion (not shown in FIG. 13) is formed. Here, in the second modification, an example in which the connection terminal portion is formed on the first inner surface 24Bd is shown. The electronic component 50*a* is mounted on the connection terminal portion. At this time, the electronic component 50*a* is housed in the recessed portion 24Ba for component mounting in such a form as not externally projecting from the first surface [I] and the sixth surface [VI].

With such a state, a gap 24Bc with a predetermined distance is provided between the surface (second inner surface 24Be) where the connection terminal portion is not formed, of the first inner surface 24Bd and the second inner surface 24Be, and the electronic component 50*a* mounted in the recessed portion 24Ba for component mounting. Further, in the second modification, the gap 24Bc with a predetermined distance is also provided between the electronic component 50*a* and the wall surface 24Bf.

The gap 24Bc and an outer surface side of the electronic component 50*a* are filled with the sealing resin 70. In this manner, the electronic component 50*a* including the connecting portion with the three-dimensional circuit board 24B is sealed with the sealing resin 70. The other configurations are substantially the same as the configurations of the aforementioned first modification.

According to the second modification configured as described above, exactly the same effects as the effects of the aforementioned embodiment and first modification can be obtained. In the second modification, the recessed portion 24Ba for component mounting is formed in a groove shape from the second surface [II] toward the third surface [III] (in the direction orthogonal to the optical axis) and so as to include the wall surface 24Bf parallel to the second surface [II]. In the second modification, since the recessed portion 24Ba for component mounting is formed as such, a filling amount of the sealing resin 70 can be reduced. In addition, since widespread wetting with the sealing resin 70 can be restricted, the filling amount is easily controlled.

Further, in the second modification, since the gap 24Bc is also provided between the electronic component 50*a* and the wall surface 24Bf, the connecting portion of the electronic component 50*a* can be more firmly reinforced.

Note that in the second modification, a configuration example in which the recessed portion 24Ba for component mounting is provided in the site where the first surface [I] and the sixth surface [VI] cross each other has been illustrated, but the configuration of the three-dimensional circuit board is not limited to the configuration example. For example, the configuration may be made such that the recessed portion 24Ba for component mounting is provided in a site where the fourth surface [IV] and the sixth surface [VI] cross each other. Such a configuration example can also obtain exactly the same effects as the effects of the second modification.

Further, in the second modification, a configuration example is made such that the recessed portion 24Ba for component mounting in a groove shape from the second surface [II] toward the third surface [III] is provided. In other words, in the second modification, the recessed portion 24Ba for component mounting is provided in a site facing the second surface III, but the configuration of the three-dimensional circuit board is not limited to the configuration example. For example, the configuration may be made such that the recessed portion 24Ba for component mounting is formed in a groove shape from the third surface [III] toward the second surface [II] and is provided in a site facing the third surface [III]. Such a configuration example can also obtain exactly the same effects as the effects of the second modification.

Furthermore, in the second modification, a configuration example is made such that the connection terminal portion is formed on the first inner surface 24Bd and the gap 24Bc is provided on the second inner surface 24Be, but the configuration of the three-dimensional circuit board is not limited to the configuration example, as with the first modification. Therefore, for example, in the second modification, the configuration may be such that the gap 24Bc is provided on the first inner surface 24Bd and the connection terminal portion is formed on the second inner surface 24Be. Such a configuration example can also obtain exactly the same effects as the effects of the second modification.

[Third Modification]

Figure 14:
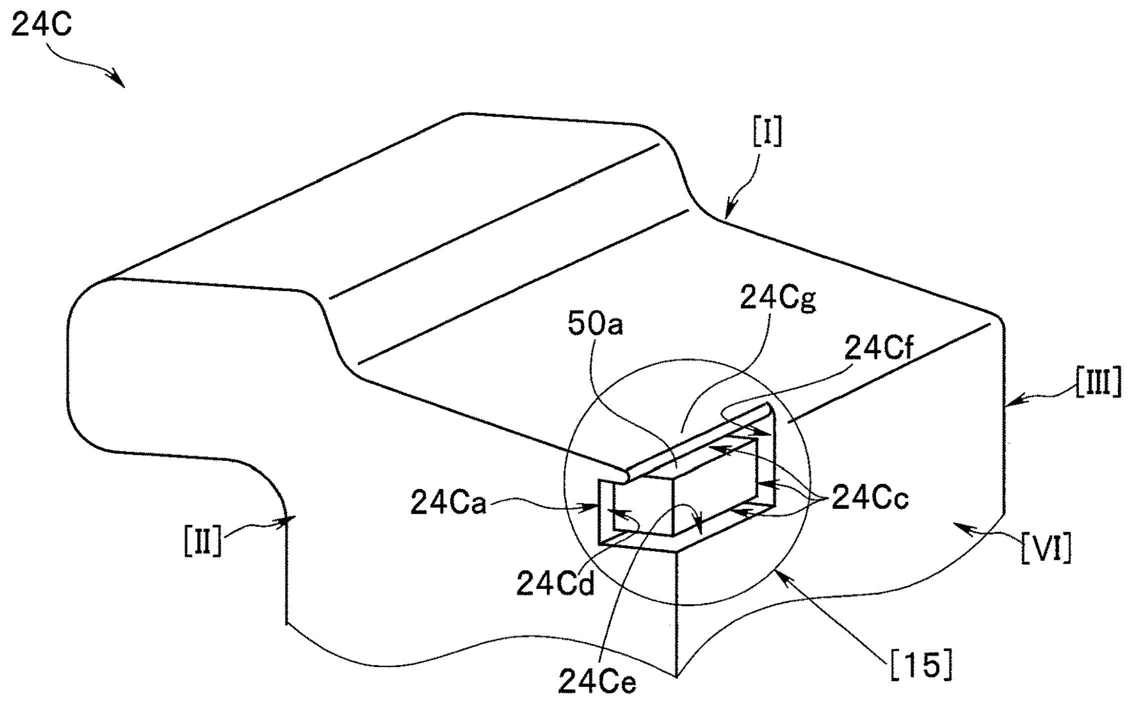
FIG. 14 is a view showing a portion of an outer shape of a portion, which is cut out, of the three-dimensional circuit board of a third modification of the three-dimensional circuit board in the image pickup unit of the embodiment of the present invention.
Figure 15:
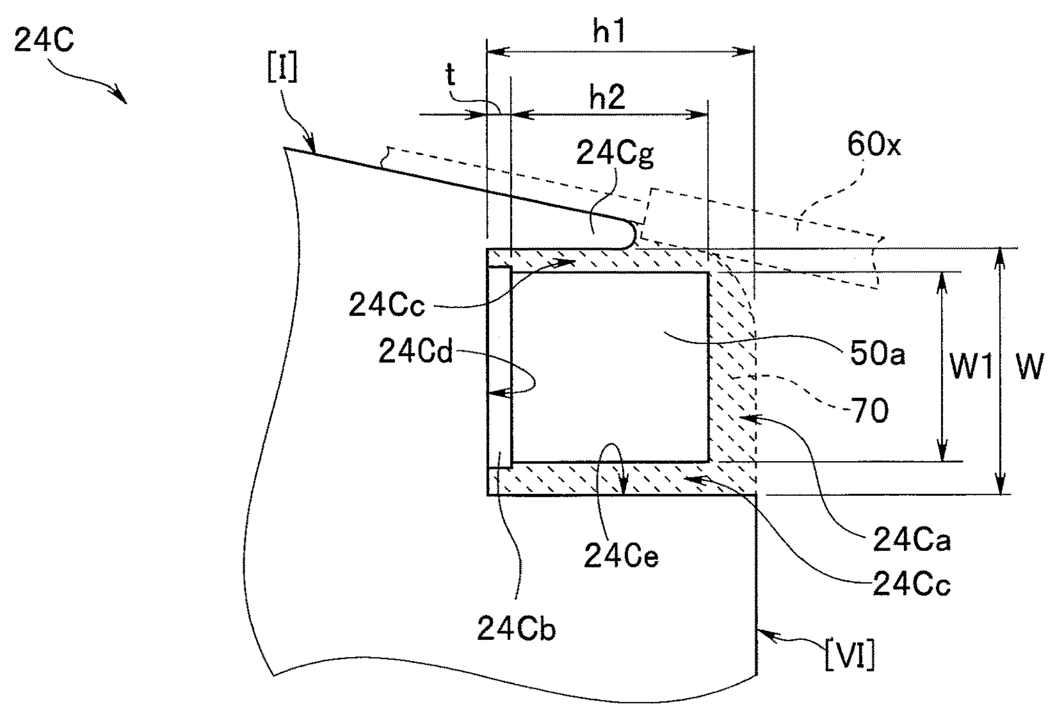
FIG. 15 is a view showing an enlarged right side surface of a portion depicted by reference numeral [15] of FIG. 14.

Next, a third modification of the three-dimensional circuit board in the image pickup unit of the embodiment of the present invention is described with reference to FIG. 14 and FIG. 15. FIG. 14 illustrates a portion of an outer shape of a portion, which is cut out, of the three-dimensional circuit board of the third modification. Therefore, in FIG. 14, illustration of the connection electrodes 24*x* formed on the outer surface of the three-dimensional circuit board is omitted. FIG. 15 is a view showing an enlarged right side surface of a portion depicted by reference numeral [15] of FIG. 14.

A basic configuration of the third modification is substantially the same as the configurations of the aforementioned embodiment and first and second modifications. In the third modification, the form of a recessed portion 24Ca for component mounting of a three-dimensional circuit board 24C is the only difference from the second modification. Therefore, in the following description, illustration of the same constituent members as the constituent members of the aforementioned embodiment and first and second modifications is omitted, and description of the same constituent members is omitted. Only the portions different from the portions of the aforementioned embodiment and first and second modifications are described below.

As shown in FIG. 14 and FIG. 15, the three-dimensional circuit board 24C in the third modification is similar to the first and the second modifications in that the recessed portion 24Ca for component mounting is formed in the site where the first surface [I] and the sixth surface [VI] cross each other. In other words, the recessed portion 24Ca for component mounting is in a form in which a portion of each of the first surface [I] and the sixth surface [VI] is cut out.

However, in the third modification, as shown in FIG. 14, the recessed portion 24Ca for component mounting is formed in a groove shape from the second surface [II] toward the third surface [III] (in the direction orthogonal to the optical axis) and so as to include a wall surface 24Cf parallel to the second surface [II]. Further, in the third modification, the recessed portion 24Ca for component mounting is formed so as to include an eaves portion 24Cg in a site facing the first surface [I]. The eaves portion 24Cg is a site formed such that the first surface II extends toward the back surface side. The eaves portion 24Cg is a site covering a part of an opening portion, which faces the first surface [I], of the recessed portion 24Ca for component mounting. A distal end portion of the eaves portion 24Cg is round-chamfered.

With such a configuration, in the third modification, the recessed portion 24Ca for component mounting includes two surfaces (first inner surface 24Cd, second inner surface 24Ce) facing an outer surface of the three-dimensional circuit board 24C, the wall surface 24Cf, and the eaves portion 24Cg. At least one electronic component 50*a* is mounted in the recessed portion 24Ca for component mounting.

Here, on either one of the two surfaces (24Cd, 24Ce) of the recessed portion 24Ca for component mounting, a connection terminal portion 24Cb (not shown in FIG. 14; see FIG. 15) is formed. Note that in the third modification, an example in which the connection terminal portion 24Cb is formed on the first inner surface 24Cd is shown. The electronic component 50*a* is mounted on the connection terminal portion 24Cb. At this time, the electronic component 50*a* is housed in the recessed portion 24Ca for component mounting in such a form as not externally projecting from the first surface [I] and the sixth surface [VI].

With such a state, a gap 24Cc with a predetermined distance is provided between the surface (second inner surface 24Ce) where the connection terminal portion 24Cb is not formed, of the first inner surface 24Cd and the second inner surface 24Ce, and the electronic component 50*a* mounted in the recessed portion 24Ca for component mounting. The gap 24Cc with a predetermined distance is also provided between the electronic component 50*a* and the wall surface 24Cf. Further, in the third modification, the gap 24Cc with a predetermined distance is also provided between the electronic component 50*a* and an inner surface of the eaves portion 24Cg.

The gap 24Cc and an outer surface side of the electronic component 50*a* are filled with the sealing resin 70. In this manner, the electronic component 50*a* including the connecting portion with the three-dimensional circuit board 24C is sealed with the sealing resin 70. The other configurations are substantially the same as the configurations of the aforementioned second modification.

According to the third modification configured as described above, exactly the same effects as the effects of the aforementioned second modification can be obtained. In the third modification, the recessed portion 24Ca for component mounting is formed so as to further include the eaves portion 24Cg covering the part of the opening portion, which faces the first surface [I]. With such a configuration, in the third modification, since the gap 24Cc can also be provided between the electronic component 50*a* and the inner surface of the eaves portion 24Cg, the connecting portion of the electronic component 50*a* can be more firmly reinforced.

In the third modification, since the distal end portion of the eaves portion 24Cg is round-chamfered, even when the core wire of the cable 60*x* (see FIG. 15) connected to the first surface [I] contacts the distal end portion of the eaves portion 24Cg, the core wire can be prevented from breaking.

For example, in a case where a predetermined load is applied to the cable 60*x* with the core wire of the cable 60*x* (see FIG. 15) in contact with the distal end portion of the eaves portion 24Cg, the core wire of the cable 60*x* slides in the distal end portion of the eaves portion 24Cg. At this time, in a case where the distal end portion of the eaves portion 24Cg is formed with an acute corner portion, the core wire could break, and thus, in the third modification, since the distal end portion of the eaves portion 24Cg is round-chamfered, the core wire of the cable 60*x* can be prevented from breaking.

In a case where the cable 60*x* is connected by soldering to the first surface [I] and the fourth surface [IV] after mounting the electronic component 50*a* on the recessed portion 24Ca for component mounting of the three-dimensional circuit board 24C, a soldering iron is brought into contact with a connecting portion between the connection electrode 24*x* on the first surface [I] or the fourth surface [IV] and the core wire of the cable 60*x*. At this time, in the configuration of the third modification, the eaves portion 24Cg is present between the soldering iron and the electronic component 50*a* within the recessed portion 24Ca for component mounting.

Thus, the heat of the soldering iron is unlikely to be transmitted to the electronic component 50*a* within the recessed portion 24Ca for component mounting by means of the eaves portion 24Cg. Therefore, in the configuration of the third modification, with the eaves portion 24Cg provided, the solder in the connecting portion of the electronic component 50*a* connected by soldering within the recessed portion 24Ca for component mounting can be prevented from remelting.

Note that in the third modification, a configuration example in which the recessed portion 24Ca for component mounting is provided in the site where the first surface [I] and the sixth surface [VI] cross each other and the eaves portion 24Cg formed such that the first surface [I] extends toward the back surface side is provided has been illustrated, but the configuration of the three-dimensional circuit board is not limited to the configuration example. For example, the configuration may be made such that the recessed portion 24Ca for component mounting is provided in a site where the fourth surface [IV] and the sixth surface [VI] cross each other and the eaves portion 24Cg formed such that the fourth surface [IV] extends toward the back surface side is provided. Such a configuration example can also obtain exactly the same effects as the effects of the third modification.

In the third modification, a configuration example is made such that the recessed portion 24Ca for component mounting is provided in the site facing the second surface [II], as with the second modification, but the configuration of the three-dimensional circuit board is not limited to the configuration example. For example, the configuration may be made such that the recessed portion 24Ca for component mounting is provided in a site facing the third surface [III]. Such a configuration example can also obtain exactly the same effects as the effects of the third modification.

Further, in the third modification, a configuration example is made such that the connection terminal portion 24Cb is formed on the first inner surface 24Cd and the gap 24Cc is provided on the second inner surface 24Ce, but the configuration of the three-dimensional circuit board is not limited to the configuration example, as with the first and the second modifications. Therefore, for example, in the third modification, the configuration may be such that the gap 24Cc is provided on the first inner surface 24Cd and the connection terminal portion 24Cb is formed on the second inner surface 24Ce. Such a configuration example can also obtain exactly the same effects as the effects of the third modification.

[Fourth Modification]

Figure 16:
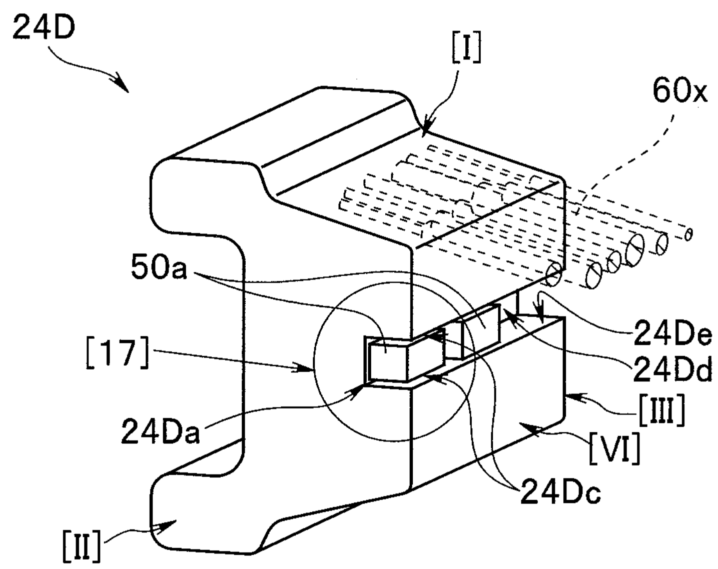
FIG. 16 is a view showing an outer shape of the three-dimensional circuit board, which is extracted alone, of a fourth modification of the three-dimensional circuit board in the image pickup unit of the embodiment of the present invention.
Figure 17:
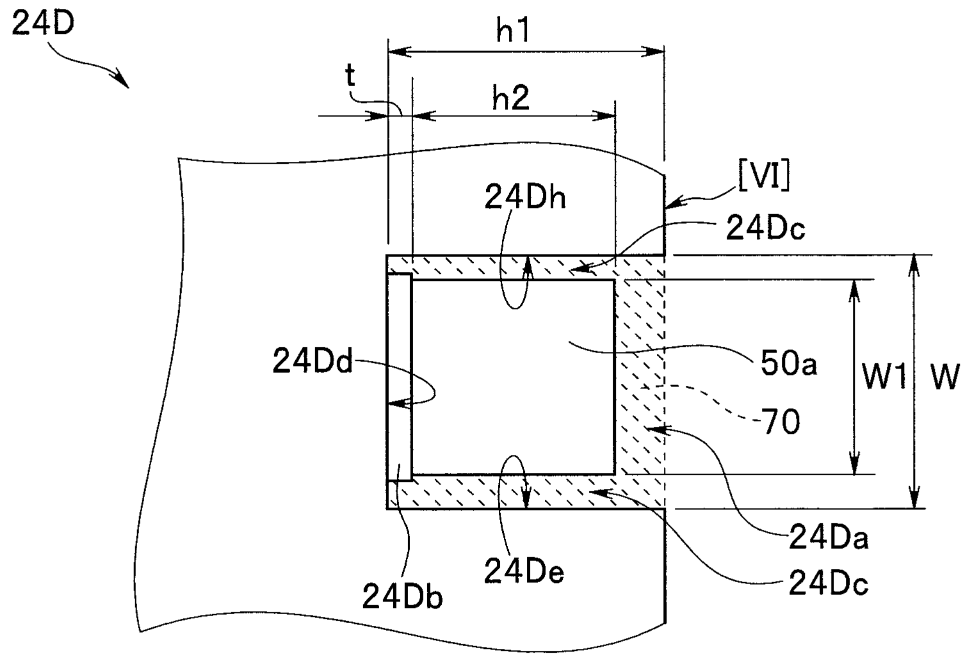
FIG. 17 is a view showing an enlarged right side surface of a portion depicted by reference numeral [17] of FIG. 16.

Next, FIG. 16 and FIG. 17 are views showing a fourth modification of the three-dimensional circuit board in the image pickup unit of the embodiment of the present invention. FIG. 16 illustrates an outer shape of the three-dimensional circuit board, which is extracted alone, of the fourth modification. Therefore, in FIG. 16, illustration of the connection electrodes 24*x* formed on the outer surface of the three-dimensional circuit board is omitted. FIG. 17 is a view showing an enlarged right side surface of a portion depicted by reference numeral [17] of FIG. 16.

A basic configuration of the fourth modification is substantially the same as the configurations of the aforementioned embodiment and first modification. In the fourth modification, the arrangement of a recessed portion 24Da for component mounting of a three-dimensional circuit board 24D is the only difference. Therefore, in the following description, illustration of the same constituent members as the constituent members of the aforementioned embodiment and first modification is omitted, and description of the same constituent members is omitted. Only the portions different from the portions of the aforementioned embodiment and first modification are described below.

As shown in FIG. 16 and FIG. 17, in the three-dimensional circuit board 24D in the fourth modification, the recessed portion 24Da for component mounting is formed on the sixth surface [VI]. As shown in FIG. 16, the recessed portion 24Da for component mounting is formed in a groove shape that is inserted from the second surface [II] through the third surface [III] (in a direction orthogonal to the optical axis). At least one electronic component 50*a* is mounted in the recessed portion 24Da for component mounting. Note that in the fourth modification, an example in which two electronic components 50*a* are mounted is shown.

As shown in FIG. 17, the recessed portion 24Da for component mounting includes a groove bottom surface 24Dd and two wall surfaces (24De, 24Dh) that are orthogonal to the groove bottom surface 24Dd. The groove bottom surface 24Dd is a surface forming a bottom surface of the recessed portion 24Da for component mounting in a groove shape. The groove bottom surface 24Dd is a surface parallel to the sixth surface [VI]. The two wall surfaces (24De, 24Dh) are disposed at positions facing each other with a predetermined distance, are both orthogonal to the sixth surface [VI], and are surfaces orthogonal to the groove bottom surface 24Dd. Note that the distance at which the two wall surfaces (24De, 24Dh) are spaced apart corresponds to the groove width W of the recessed portion 24Da for component mounting. Here, the groove width W of the recessed portion 24Da for component mounting is set larger than the width dimension W1 of the electronic component 50*a*.

A connection terminal portion 24Db (not shown in FIG. 16; see FIG. 17) is formed on the groove bottom surface 24Dd of the recessed portion 24Da for component mounting. The electronic component 50*a* is mounted on the connection terminal portion 24Db. At this time, the electronic component 50*a* is housed in the recessed portion 24Da for component mounting in such a form as not externally projecting from the sixth surface [VI]. In other words, the depth dimension h1 of the recessed portion 24Da for component mounting is set larger than a dimension of the height dimension h2 of the electronic component with the thickness dimension t of the connection terminal portion added ($h1 \geq h2+t$).

A gap 24Dc with a predetermined distance is provided between each of the two wall surfaces (24De, 24Dh) and the electronic component 50*a* mounted in the recessed portion 24Da for component mounting. The gap 24Dc and an outer surface side of the electronic component 50*a* are filled with the sealing resin 70. In this manner, the electronic component 50*a* including the connecting portion with the three-dimensional circuit board 24D is sealed with the sealing resin 70. The other configurations are substantially the same as the configurations of the aforementioned first modification.

According to the fourth modification configured as described above, substantially the same effects as the effects of the aforementioned embodiment, first modification, and the like can be obtained. In the fourth modification, the three-dimensional circuit board 24D is configured such that the recessed portion 24Da for component mounting is formed on the sixth surface [VI], the connection terminal portion 24Db is provided on the groove bottom surface 24Dd in the recessed portion 24Da for component mounting, and the two wall surfaces 24De, 24Dh each facing the electronic component 50*a* are provided. The configuration is made such that the gap 24Dc is provided in the site where the electronic component 50*a* and the two wall surfaces 24De, 24Dh face each other.

In this manner, in exactly the same manner as the third modification, when the cable 60*x* is connected by soldering to the first surface [I] or the fourth surface [IV], the transfer of the heat of the soldering iron to the electronic component 50*a* housed in the recessed portion 24Da for component mounting can be restricted. Simultaneously, since the gap 24Dc can be filled with the sealing resin 70, the outer surface of the electronic component 50*a* including the connecting portion with the three-dimensional circuit board 24D can be filled with the sealing resin 70.

Further, in the configuration of the fourth modification, since the configuration is made such that the electronic component 50*a* is mounted on the groove bottom surface 24Dd that is the surface orthogonal to the optical axis, and is thus in the same arrangement direction of the constituent members constituting the image pickup unit, that is, the image pickup device, the flat circuit board, and the three-dimensional circuit board 24D, thereby being capable of simplifying the manufacturing process and accordingly contributing to reducing manhours in manufacturing.

The present invention is not limited to the aforementioned embodiment, and it goes without saying that it is possible to carry out various modifications and applications within the scope without departing from the gist of the invention. In the aforementioned embodiment, the inventions in various phases are included, and various inventions can be extracted by appropriate combinations of a plurality of constituent elements disclosed. For example, when the problem to be solved by the invention can still be solved and the advantageous effects of the invention can be obtained even if some constituent elements are deleted from all the constituent elements shown in the aforementioned embodiment, a configuration without such deleted constituent elements can be extracted as the invention. Further, the constituent elements across different embodiments may be appropriately combined. The present invention is not restricted by any specific embodiments other than what is specified by the attached claims.

What is claimed is:

1. An image pickup unit comprising: an image pickup device comprising an image sensor; a flat circuit board connected to a back surface of the image pickup device; a three-dimensional circuit board connected to a back surface of the flat circuit board; a plurality of electronic components mounted on the flat circuit board and on the three-dimensional circuit board; and a plurality of cables connected to the three-dimensional circuit board, wherein the three-dimensional circuit board includes: a first surface; a second surface substantially orthogonal to the first surface; a third surface facing opposite to the second surface; a fourth surface facing opposite to the first surface; a fifth surface facing the back surface of the flat circuit board; and a sixth surface facing opposite to the fifth surface, wherein the three-dimensional circuit board having a recess on at least one of the first surface, the second surface, the third surface, the fourth surface, the fifth surface and the sixth surface, and the recess having a connection terminal portion disposed in a part of an inner surface of the recess, at least one of the plurality of electronic components or the plurality of cables is mounted on or connected to the connection terminal portion of the recess of the three-dimensional circuit board, the recess is arranged, at a position where the first surface and the sixth surface cross each other, from the second surface toward the third surface, the recess having a wall surface parallel to the second surface, and at least one of the electronic components is mounted in the recess.

2. The image pickup unit according to claim 1, wherein each of the electronic components does not externally project from the sixth surface.

3. The image pickup unit according to claim 1, wherein the recess being defined by at least two wall surfaces, and a gap with a predetermined distance is provided between at least one of the two wall surfaces and each of the electronic components mounted in the recess.

4. The image pickup unit according to claim 3, wherein the gap is filled with resin.

5. The image pickup unit according to claim 1, further comprising an eave extending from the first surface toward the sixth surface, the eave overhanging at least a portion of the recess.

6. The image pickup unit according to claim 5, wherein a distal end edge of the eave is round-chamfered.

7. An image pickup unit comprising: an image pickup device comprising an image sensor; a flat circuit board connected to a back surface of the image pickup device; a three-dimensional circuit board connected to a back surface of the flat circuit board; a plurality of electronic components mounted on the flat circuit board and on the three-dimensional circuit board; and a plurality of cables connected to the three-dimensional circuit board, wherein the three-dimensional circuit board includes: a first surface; a second surface substantially orthogonal to the first surface; a third surface facing opposite to the second surface; a fourth surface facing opposite to the first surface; a fifth surface facing the back surface of the flat circuit board; and a sixth surface facing opposite to the fifth surface, wherein the three-dimensional circuit board having a recess on at least one of the first surface, the second surface, the third surface, the fourth surface, the fifth surface and the sixth surface, and the recess having a connection terminal portion disposed in a part of an inner surface of the recess, at least one of the plurality of electronic components or the plurality of cables is mounted on or connected to the connection terminal portion of the recess of the three-dimensional circuit board, the recess is arranged at a position where the first surface and the sixth surface cross each other, the first surface having an eave extending toward the sixth surface side and overhanging at least a portion of the recess, and at least one of the electronic components is mounted in the recess.

8. The image pickup unit according to claim 7, wherein a distal end edge of the eave is round-chamfered.

9. The image pickup unit according to claim 7, wherein each of the electronic components does not externally project from the sixth surface.

10. The image pickup unit according to claim 7, wherein the recess being defined by at least two wall surfaces, and a gap with a predetermined distance is provided between at least one of the two wall surfaces and each of the electronic components mounted in the recess.

11. The image pickup unit according to claim 10, wherein the gap is filled with resin.

12. An endoscope comprising: an insertion portion, and an image pickup unit disposed within a distal end portion of the insertion portion, the image pickup unit comprises: an image pickup device comprising an image sensor; a flat circuit board connected to a back surface of the image pickup device; a three-dimensional circuit board connected to a back surface of the flat circuit board; a plurality of electronic components mounted on the flat circuit board and on the three-dimensional circuit board; and a plurality of cables connected to the three-dimensional circuit board, wherein the three-dimensional circuit board includes: a first surface; a second surface substantially orthogonal to the first surface; a third surface facing opposite to the second surface; a fourth surface facing opposite to the first surface; a fifth surface facing the back surface of the flat circuit board; and a sixth surface facing opposite to the fifth surface, wherein the three-dimensional circuit board having a recess on at least one of the first surface, the second surface, the third surface, the fourth surface, the fifth surface and the sixth surface, and the recess having a connection terminal portion disposed in a part of an inner surface of the recess, at least one of the plurality of electronic components or the plurality of cables is mounted on or connected to the connection terminal portion of the recess of the three-dimensional circuit board, the recess is arranged at a position where the first surface and the sixth surface cross each other, from the second surface toward the third surface, the recess having a wall surface parallel to the second surface, and at least one of the electronic components is mounted in the recess.

13. The endoscope according to claim 12, wherein each of the electronic components does not externally project from the sixth surface.

14. The endoscope according to claim 12, wherein the recess being defined by at least two wall surfaces, and a gap with a predetermined distance is provided between at least one of the two wall surfaces and each of the electronic components mounted in the recess.

15. The endoscope according to claim 14, wherein the gap is filled with resin.

16. The endoscope according to claim 12, further comprising an eave extending from the first surface toward the sixth surface, the eave overhanging at least a portion of the recess.

17. The endoscope according to claim 16, wherein a distal end edge of the eave is round-chamfered.

* * * * *